US009920308B2

(12) United States Patent
Margeot et al.

(10) Patent No.: US 9,920,308 B2
(45) Date of Patent: Mar. 20, 2018

(54) ENDOGLUCANASE VARIANTS HAVING IMPROVED ACTIVITY, AND USES OF SAME

(71) Applicants: IFP ENERGIES NOUVELLES, Rueil Malmaison (FR); PROTEUS, Longjumeau (FR); CENTRE NATIONAL DE LA RECHERCHE SCIENTIFIQUE—CNRS, Paris (FR)

(72) Inventors: Antoine Margeot, Paris (FR); Senta Blanquet, Fourqueux (FR); Cecile Persillon, Nimes (FR); Celine Ayrinhac, Domessargues (FR); Christophe Ullmann, Nimes (FR); Olivier Bonzom, Nimes (FR); Sebastien Fort, Vaulnaveys-le-Haut (FR); Sylvie Armand, Grenoble (FR); Marine Lenon, Sassenage (FR); Maud Petit, Marcq en Baroeul (FR)

(73) Assignees: IFP ENERGIES NOUVELLES, Rueil Malmaison (FR); PROTEUS, Longjiumeau (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 0 days.

(21) Appl. No.: 15/038,614

(22) PCT Filed: Nov. 21, 2014

(86) PCT No.: PCT/FR2014/052985

§ 371 (c)(1),
(2) Date: May 23, 2016

(87) PCT Pub. No.: WO2015/075392

PCT Pub. Date: May 28, 2015

(65) Prior Publication Data

US 2016/0289661 A1 Oct. 6, 2016

(30) Foreign Application Priority Data

Nov. 22, 2013 (FR) ..................................... 13 61511

(51) Int. Cl.
*C12N 9/42* (2006.01)
*C12P 7/10* (2006.01)
*D21C 5/00* (2006.01)

(52) U.S. Cl.
CPC .............. *C12N 9/2437* (2013.01); *C12P 7/10* (2013.01); *C12Y 302/01004* (2013.01); *D21C 5/005* (2013.01); *Y02E 50/16* (2013.01); *Y02E 50/343* (2013.01)

(58) Field of Classification Search
None
See application file for complete search history.

(56) References Cited

FOREIGN PATENT DOCUMENTS

| | | |
|---|---|---|
| WO | 2008/088724 | 7/2008 |
| WO | 2011/153516 | 12/2011 |
| WO | 2012/036810 | 3/2012 |
| WO | 2013/096244 | 6/2013 |

OTHER PUBLICATIONS

Accession Q7Z7X2. Oct. 1, 2003.*
Accession G0RB67. Oct. 19, 2011.*
Qin et al. J Biotechnol. Jun. 1, 2008;135(2):190-5.*
Kataria et al. Bioresour Technol. Nov. 2011;102(21):9970-5.*
The International Search Report (ISR) with Written Opinion for PCT/FR2014/052985 dated Mar. 2, 2015, pp. 1-13.
English Translation of the ISR for PCT/FR2014/052985 dated Mar. 2, 2015, pp. 1-3.

* cited by examiner

*Primary Examiner* — Christian Fronda
(74) *Attorney, Agent, or Firm* — McDonnell Boehnen Hulbert & Berghoff

(57) ABSTRACT

The present invention relates to the expression and optimization of enzymes involved in the breakdown of lignocellulosic biomass. The present invention relates more specifically to variants of *Trichoderma reesei* endoglucanase II, and the use of said variants having an improved performance in methods of breaking down cellulose and producing biofuel.

17 Claims, 3 Drawing Sheets

SEQUENCE LISTING

```
<160> NUMBER OF SEQ ID NOS: 38

<210> SEQ ID NO 1
<211> LENGTH: 1257
<212> TYPE: DNA
<213> ORGANISM: Trichoderma reesei

<400> SEQUENCE: 1

atgaacaagt ccgtggctcc attgctgctt gcagcgtcca tactatatgg cggcgccgct     60

gcacagcaga ctgtctgggg ccagtgtgga ggtattggtt ggagcggacc tacgaattgt    120

gctcctggct cagcttgttc gaccctcaat ccttattatg cgcaatgtat tccgggagcc    180

actactatca ccacttcgac ccggccacca tccggtccaa ccaccaccac cagggctacc    240

tcaacaagct catcaactcc acccacgagc tctggggtcc gatttgccgg cgttaacatc    300

gcgggttttg actttggctg taccacagat ggcacttgcg ttacctcgaa ggtttatcct    360

ccgttgaaga acttcaccgg ctcaaacaac taccccgatg gcatcggcca gatgcagcac    420

ttcgtcaacg acgacgggat gactattttc cgcttacctg tcggatggca gtacctcgtc    480

aacaacaatt tgggcggcaa tcttgattcc acgagcattt ccaagtatga tcagcttgtt    540

caggggtgcc tgtctctggg cgcatactgc atcgtcgaca tccacaatta tgctcgatgg    600

aacggtggga tcattggtca gggcggccct actaatgctc aattcacgag cctttggtcg    660

cagttggcat caaagtacgc atctcagtcg agggtgtggt tcggcatcat gaatgagccc    720

cacgacgtga acatcaacac ctgggctgcc acggtccaag aggttgtaac cgcaatccgc    780

aacgctggtg ctacgtcgca attcatctct ttgcctggaa atgattggca atctgctggg    840

gctttcatat ccgatggcag tgcagccgcc ctgtctcaag tcacgaaccc ggatgggtca    900

acaacgaatc tgatttttga cgtgcacaaa tacttggact cagacaactc cggtactcac    960

gccgaatgta ctacaaataa cattgacggc gccttttctc cgcttgccac ttggctccga   1020
```

```
cagaacaatc gccaggctat cctgacagaa accggtggtg gcaacgttca gtcctgcata   1080

caagacatgt gccagcaaat ccaatatctc aaccagaact cagatgtcta tcttggctat   1140

gttggttggg gtgccggatc atttgatagc acgtatgtcc tgacggaaac accgactggc   1200

agtggtaact catggacgga cacatccttg gtcagctcgt gtctagcaag aaagtag      1257


<210> SEQ ID NO 2
<211> LENGTH: 418
<212> TYPE: PRT
<213> ORGANISM: Trichoderma reesei

<400> SEQUENCE: 2

Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335
```

```
Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys
```

<210> SEQ ID NO 3
<211> LENGTH: 1257
<212> TYPE: DNA
<213> ORGANISM: Artificial Sequence
<220> FEATURE:
<223> OTHER INFORMATION: 37D12

<400> SEQUENCE: 3

```
atgaacaagt ccgtggctcc attgctgctt gcagcgtcca tactatatgg cggcgccgct     60

gcacagcaga ctgtctgggg ccagtgtgga ggtattggtt ggagcggacc tacgaattgt    120

gctcctggct cagcttgttc gaccctcaat ccttattatg cgcaatgtat tccgggagcc    180

actactatca ccacttcgac ccggccacca tccggtccaa ccaccaccac cagggctacc    240

tcaacaagct catcaactcc acccacgagc tctggggtcc gatttgccgg cgttaacatc    300

gcgggttttg actttggctg taccacagat ggcacttgcg ttacctcgaa ggtttatcct    360

ccgttgaaga acttcaccgg ctcaaacaac taccccgatg gcatcggcca gatgcagcac    420

ttcgtcaacg acgacgggat gactattttc cgcttacctg tcggatggca gtacctcgtc    480

aacaacaatt tgggcggcaa tcttgattcc acgagcattt ccaagtatga tcagcttgtt    540

caggggtgcc tgtctctggg cgcatactgc atcgtcgaca tccacaatta tgctcgatgg    600

aacggtggga tcattggtca gggcggccct actaatgctc aattcacgag cctttggtcg    660

cagttggcat caaagtacgc atctcagtcg agggtgtggt tcggcatcat gaatgagccc    720

cacgacgtga acatcaacac ctgggctgcc acggtccaag aggttgtaac cgcaatccgc    780

aacgctggtg ctacgtcgca attcatctct ttgcctggaa atgattggca atctgctggg    840

gctttcatat ccgatggcag tgcagccgcc ctgtctcaag tcacgaaccc ggatgggtca    900

acaacgaatc tgatttttga cgtgcacaaa tacttggact cagacaactc cggtactcac    960

gccgaatgtg taacaaataa cattgacgcc gcctttgcac cgcttgccac ttggctccga   1020

gcaaacggtc gccaggctat cctgagcgaa accggtggtg gcaacaccgc gtcctgccag   1080

acatatttgt gccagcaagt tgcttatctc aacgcaaact cagatgtcta tcttggctat   1140

attggttggt ctgccggatc atttgatagc acgtatattc tgacggaaac accgaatggc   1200

agtggtaact catggacgga cacatccttg gtcagctcgt gtctagcaag aaagtag      1257
```

<210> SEQ ID NO 4
<211> LENGTH: 418
<212> TYPE: PRT
<213> ORGANISM: Artificial Sequence
<220> FEATURE:
<223> OTHER INFORMATION: 37D12

<400> SEQUENCE: 4

-continued

```
Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Val Thr Asn Asn Ile Asp Ala Ala Phe Ala Pro Leu Ala
                325                 330                 335

Thr Trp Leu Arg Ala Asn Gly Arg Gln Ala Ile Leu Ser Glu Thr Gly
            340                 345                 350

Gly Gly Asn Thr Ala Ser Cys Gln Thr Tyr Leu Cys Gln Gln Val Ala
        355                 360                 365

Tyr Leu Asn Ala Asn Ser Asp Val Tyr Leu Gly Tyr Ile Gly Trp Ser
    370                 375                 380

Ala Gly Ser Phe Asp Ser Thr Tyr Ile Leu Thr Glu Thr Pro Asn Gly
385                 390                 395                 400

Ser Gly Asn Ser Trp Thr Asp Thr Ser Leu Val Ser Ser Cys Leu Ala
                405                 410                 415

Arg Lys
```

<210> SEQ ID NO 5
<211> LENGTH: 1260
<212> TYPE: DNA
<213> ORGANISM: Artificial Sequence
<220> FEATURE:
<223> OTHER INFORMATION: 45A7

<400> SEQUENCE: 5
atgaacaagt ccgtggctcc attgctgctt gcagcgtcca tactatatgg cggcgccgct 60
gcacagcaga ctgtctgggg ccagtgtgga ggtattggtt ggagcggacc tacgaattgt 120
gctcctggct cagcttgttc gaccctcaat ccttattatg cgcaatgtat tccgggagcc 180
actactatca ccacttcgac ccggccacca tccggtccaa ccaccaccac cagggctacc 240
tcaacaagct catcaactcc acccacgagc tctggggtcc gatttgccgg cgttaacatc 300
gcgggttttg actttggctg taccacagat ggcacttgcg ttacctcgaa ggtttatcct 360
ccgttgaaga acttcaccgg ctcaaacaac taccccgatg gcatcggcca gatgcagcac 420
ttcgtcaacg acgacgggat gactattttc cgcttacctg tcggatggca gtacctcgtc 480
aacaacaatt tgggcggcaa tcttgattcc acgagcattt ccaagtatga tcagcttgtt 540
caggggtgcc tgtctctggg cgcatactgc atcgtcgaca tccacaatta tgctcgatgg 600
aacggtggga tcattggtca gggcggccct actaatgctc aattcacgag cctttggtcg 660
cagttggcat caaagtacgc atctcagtcg agggtgtggt tcggcatcat gaatgagccc 720
cacgacgtga acatcaacac ctgggctgcc acggtccaag aggttgtaac cgcaatccgc 780
aacgctggtg ctacgtcgca attcatctct ttgcctggaa atgattggca atctgctggg 840
gctttcatat ccgatggcag tgcagccgcc ctgtctcaag tcacgaaccc ggatgggtca 900
acaacgaatc tgatttttga cgtgcacaaa tacttggact cagacaactc cggtactcac 960
gccgaatgtg taacaaataa cattgacgcc gcctttgcac cgcttgccac ttggctccga 1020
gcaaacggac gccaggctat cctgacagaa accggtggtg gcaacaccgc gtcctgccag 1080
acatatttgt gccagcaagt tgcttatctc aacgcaaact cagatgtcta tcttggctat 1140
attggttggt ctgccggatc atttgatagc acgtatattc tgacggaaac accgaatggc 1200
agtggttctt caatgacgga ccaagcgttg gtcgcggctt gtctaactag aacatcgtag 1260

<210> SEQ ID NO 6
<211> LENGTH: 419
<212> TYPE: PRT
<213> ORGANISM: Artificial Sequence
<220> FEATURE:
<223> OTHER INFORMATION: 45A7

<400> SEQUENCE: 6

```
Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
```

```
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Val Thr Asn Asn Ile Asp Ala Ala Phe Ala Pro Leu Ala
                325                 330                 335

Thr Trp Leu Arg Ala Asn Gly Arg Gln Ala Ile Leu Thr Glu Thr Gly
            340                 345                 350

Gly Gly Asn Thr Ala Ser Cys Gln Thr Tyr Leu Cys Gln Gln Val Ala
        355                 360                 365

Tyr Leu Asn Ala Asn Ser Asp Val Tyr Leu Gly Tyr Ile Gly Trp Ser
    370                 375                 380

Ala Gly Ser Phe Asp Ser Thr Tyr Ile Leu Thr Glu Thr Pro Asn Gly
385                 390                 395                 400

Ser Gly Ser Ser Met Thr Asp Gln Ala Leu Val Ala Ala Cys Leu Thr
                405                 410                 415

Arg Thr Ser


<210> SEQ ID NO 7
<211> LENGTH: 1257
<212> TYPE: DNA
<213> ORGANISM: Artificial Sequence
<220> FEATURE:
<223> OTHER INFORMATION: 46H1

<400> SEQUENCE: 7

atgaacaagt ccgtggctcc attgctgctt gcagcgtcca tactatatgg cggcgccgct      60

gcacagcaga ctgtctgggg ccagtgtgga ggtattggtt ggagcggacc tacgaattgt     120

gctcctggct cagcttgttc gaccctcaat ccttattatg cgcaatgtat tccgggagcc     180
```

```
actactatca ccacttcgac ccggccacca tccggtccaa ccaccaccac cagggctacc    240

tcaacaagct catcaactcc acccacgagc tctggggtcc gatttgccgg cgttaacatc    300

gcgggttttg actttggctg taccacagat ggcacttgcg ttacctcgaa ggtttatcct    360

ccgttgaaga acttcaccgg ctcaaacaac taccccgatg gcatcggcca gatgcagcac    420

ttcgtcaacg acgacgggat gactattttc cgcttacctg tcggatggca gtacctcgtc    480

aacaacaatt tgggcggcaa tcttgattcc acgagcattt ccaagtatga tcagcttgtt    540

caggggtgcc tgtctctggg cgcatactgc atcgtcgaca tccacaatta tgctcgatgg    600

aacggtggga tcattggtca gggcggccct actaatgctc aattcacgag cctttggtcg    660

cagttggcat caaagtacgc atctcagtcg agggtgtggt tcggcatcat gaatgagccc    720

cacgacgtga acatcaacac ctgggctgcc acggtccaag aggttgtaac cgcaatccgc    780

aacgctggtg ctacgtcgca attcatctct ttgcctggaa atgattggca atctgctggg    840

gctttcataa ccgatggcag tgcagccgcc ctgtctcaag tcacgaaccc ggatgggtca    900

acaacgaatc tgatttttga cgtgcacaaa tacttggact cagacaactc cggtactcac    960

gccgaatgtg tgacaaataa cattgacacc gcctttgcac cgcttgccac ttggctccga   1020

cagaacaatc gccaggctat cctgacagaa accggtggtg gcaacgttca gtcctgcata   1080

caagacatgt gccagcaaat ccaatatctc aaccagaact cagatgtcta tcttggctat   1140

gttggttggg gtgccggatc atttgatagc acgtatgtcc tgacggaaac accgactggc   1200

agtggtaact catggacgga cacatccttg gtcagctcgt gtctagcaag aaagtag      1257
```

```
<210> SEQ ID NO 8
<211> LENGTH: 418
<212> TYPE: PRT
<213> ORGANISM: Artificial Sequence
<220> FEATURE:
<223> OTHER INFORMATION: 46H1

<400> SEQUENCE: 8

Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175
```

```
Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Thr Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Val Thr Asn Asn Ile Asp Thr Ala Phe Ala Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys
```

<210> SEQ ID NO 9
<211> LENGTH: 1257
<212> TYPE: DNA
<213> ORGANISM: Artificial Sequence
<220> FEATURE:
<223> OTHER INFORMATION: 50F10

<400> SEQUENCE: 9

```
atgaacaagt ccgtggctcc attgctgctt gcagcgtcca tactatatgg cggcgccgct     60

gcacagcaga ctgtctgggg ccagtgtgga ggtattggtt ggagcggacc tacgaattgt    120

gctcctggct cagcttgttc gaccctcaat ccttattatg cgcaatgtat tccgggagcc    180

actactatca ccacttcgac ccggccacca tccggtccaa ccaccaccac cagggctacc    240

tcaacaagct catcaactcc acccacgagc tctggggtcc gatttgccgg cgttaacatc    300

gcgggttttg actttggctg taccacagat ggcacttgcg ttacctcgaa ggtttatcct    360

ccgttgaaga acttcaccgg ctcaaacaac taccccgatg gcatcggcca gatgcagcac    420

ttcgtcaacg acgacgggat gactattttc cgcttacctg tcggatggca gtacctcgtc    480

aacaacaatt tgggcggcaa tcttgattcc acgagcattt ccaagtatga tcagcttgtt    540

caggggtgcc tgtctctggg cgcatactgc atcgtcgaca tccacaatta tgctcgatgg    600

aacggtggga tcattggtca gggcggccct actaatgctc aattcacgag cctttggtcg    660
```

```
cagttggcat caaagtacgc atctcagtcg agggtgtggt tcggcatcat gaatgagccc     720

cacgacgtga acatcaacac ctgggctgcc acggtccaag aggttgtaac cgcaatccgc     780

aacgctggtg ctacgtcgca attcatctct ttgcctggaa atgattggca atctgctggg     840

gctttcatat ccgatggcag tgcagccgcc ctgtctcaag tcacgaaccc ggatgggtca     900

acaacgaatc tgatttttga cgtgcacaaa tacttggact cagacaactc cggtactcac     960

gccgaatgta ctacaaataa cattgacggc gccttttctc cgcttgccac ttggctccga    1020

cagaacaatc gccaggctat cctgacagaa accggtggtg gcaacgttca gtcctgccag    1080

acatatttgt gccagcaagt tgcttatctc aacgcaaact cagatgtcta tcttggctat    1140

attggttggt ctgccggatc atttgatagc acgtatgtcc tgacggaaac accgactggc    1200

agtggtaact catggacgga cacatccttg gtcagctcgt gtctagcaag aaagtag       1257
```

<210> SEQ ID NO 10
<211> LENGTH: 418
<212> TYPE: PRT
<213> ORGANISM: Artificial Sequence
<220> FEATURE:
<223> OTHER INFORMATION: 50F10

<400> SEQUENCE: 10

```
Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255
```

```
Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Gln Thr Tyr Leu Cys Gln Gln Val Ala
        355                 360                 365

Tyr Leu Asn Ala Asn Ser Asp Val Tyr Leu Gly Tyr Ile Gly Trp Ser
    370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys


<210> SEQ ID NO 11
<211> LENGTH: 1257
<212> TYPE: DNA
<213> ORGANISM: Artificial Sequence
<220> FEATURE:
<223> OTHER INFORMATION: 108G5

<400> SEQUENCE: 11

atgaacaagt ccgtggctcc attgctgctt gcagcgtcca tactatatgg cggcgccgct      60

gcacagcaga ctgtctgggg ccagtgtgga ggtattggtt ggagcggacc tacgaattgt     120

gctcctggct cagcttgttc gaccctcaat ccttattatg cgcaatgtat tccgggagcc     180

actactatca ccacttcgac ccggccacca tccggtccaa ccaccaccac cagggctacc     240

tcaacaagct catcaactcc acccacgagc tctggggtcc gatttgccgg cgttaacatc     300

gcgggttttg actttggctg taccacagat ggcacttgcg ttacctcgaa ggtttatcct     360

ccgttgaaga acttcaccgg ctcaaacaac taccccgatg gcatcggcca gatgcagcac     420

ttcgtcaacg acgacgggat gactattttc cgcttacctg tcggatggca gtacctcgtc     480

aacaacaatt tgggcggcaa tcttgattcc acgagcattt ccaagtatga tcagcttgtt     540

caggggtgcc tgtctctggg cgcatactgc atcgtcgaca tccacaatta tgctcgatgg     600

aacggtggga tcattggtca gggcggccct actaatgctc aattcacgag cctttggtcg     660

cagttggcat caaagtacgc atctcagtcg agggtgtggt tcggcatcat gaatgagccc     720

cacgacgtga acatcaacac ctgggctgcc acggtccaag aggttgtaac cgcaatccgc     780

aacgctggtg ctacgtcgca attcatctct ttgcctggaa atgattggca atctgctggg     840

gctttcatat ccgatggcag tgcagccgcc ctgtctcaag tcacgaaccc ggatgggtca     900

acaacgaatc tgatttttga cgtgcacaaa tacttggact cagacaactc cggtactcac     960

gccgaatgta ctacaaataa cattgacggc gccttttctc cgcttgccac ttggctccga    1020

gcaaacggtc gccaggctat cctgacagaa accggtggtg gcaacgttca gtcctgcata    1080

caagacatgt gccagcaaat ccaatatctc aaccagaact cagatgtcta tcttggctat    1140
```

```
gttggttggg gtgccggatc atttgatagc acgtatgtcc tgacggaaac accgactggc   1200

agtggtaact catggacgga cacatccttg gtcagctcgt gtctagcaag aaagtag      1257


<210> SEQ ID NO 12
<211> LENGTH: 418
<212> TYPE: PRT
<213> ORGANISM: Artificial Sequence
<220> FEATURE:
<223> OTHER INFORMATION: 108G5

<400> SEQUENCE: 12

Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Ala Asn Gly Arg Gln Ala Ile Leu Thr Glu Thr Gly
```

```
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys


<210> SEQ ID NO 13
<211> LENGTH: 1257
<212> TYPE: DNA
<213> ORGANISM: Artificial Sequence
<220> FEATURE:
<223> OTHER INFORMATION: 140F7

<400> SEQUENCE: 13

atgaacaagt ccgtggctcc attgctgctt gcagcgtcca tactatatgg cggcgccgct      60

gcacagcaga ctgtctgggg ccagtgtgga ggtattggtt ggagcggacc tacgaattgt     120

gctcctggct cagcttgttc gaccctcaat ccttattatg cgcaatgtat tccgggagcc     180

actactatca ccacttcgac ccggccacca tccggtccaa ccaccaccac cagggctacc     240

tcaacaagct catcaactcc acccacgagc tctggggtcc gatttgccgg cgttaacatc     300

gcgggttttg actttggctg taccacagat ggcacttgcg ttacctcgaa ggtttatcct     360

ccgttgaaga acttcaccgg ctcaaacaac taccccgatg gcatcggcca gatgcagcac     420

ttcgtcaacg acgacgggat gactattttc cgcttacctg tcggatggca gtacctcgtc     480

aacaacgttt tgggcggcac acttgattcc aacaatttcg caacctatga ttcacttgtt     540

caggggtgcc tggcaacagg cgcaagttgc atcattgaca tccacaatta tgctcgatgg     600

aacggtggga tcattggtca gggcggccct actaatgctc aattcacgag cctttggtcg     660

cagttggcat caaagtacgc atctcagtcg agggtgtggt tcggcatcat gaatgagccc     720

cacgacgtga acatcaacac ctgggctgcc acggtccaag aggttgtaac cgcaatccgc     780

aacgctggtg ctacgtcgca attcatctct ttgcctggaa atgattggca atctgctggg     840

gctttcatat ccgatggcag tgcagccgcc ctgtctcaag tcacgaaccc ggatgggtca     900

acaacgaatc tgatttttga cgtgcacaaa tacttggact cagacaactc cggtactcac     960

gccgaatgta ctacaaataa cattgacggc gccttttctc cgcttgccac ttggctccga    1020

cagaacaatc gccaggctat cctgacagaa accggtggtg gcaacgttca gtcctgcata    1080

caagacatgt gccagcaaat ccaatatctc aaccagaact cagatgtcta tcttggctat    1140

gttggttggg gtgccggatc atttgatagc acgtatgtcc tgacggaaac accgactggc    1200

agtggtaact catggacgga cacatccttg gtcagctcgt gtctagcaag aaagtag       1257


<210> SEQ ID NO 14
<211> LENGTH: 418
<212> TYPE: PRT
<213> ORGANISM: Artificial Sequence
<220> FEATURE:
<223> OTHER INFORMATION: 140F7

<400> SEQUENCE: 14

Met Asn Lys Ser Val Ala Pro Leu Leu Leu Ala Ala Ser Ile Leu Tyr
```

-continued

```
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140

Asp Gly Met Thr Ile Phe Arg Leu Pro Val Gly Trp Gln Tyr Leu Val
145                 150                 155                 160

Asn Asn Val Leu Gly Gly Thr Leu Asp Ser Asn Asn Phe Ala Thr Tyr
                165                 170                 175

Asp Ser Leu Val Gln Gly Cys Leu Ala Thr Gly Ala Ser Cys Ile Ile
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys
```

<210> SEQ ID NO 15
<211> LENGTH: 1257
<212> TYPE: DNA
<213> ORGANISM: Artificial Sequence
<220> FEATURE:
<223> OTHER INFORMATION: 146C4

<400> SEQUENCE: 15

```
atgaacaagt ccgtggctcc attgctgctt gcagcgtcca tactatatgg cggcgccgct     60
gcacagcaga ctgtctgggg ccagtgtgga ggtattggtt ggagcggacc tacgaattgt    120
gctcctggct cagcttgttc gaccctcaat ccttattatg cgcaatgtat tccgggagcc    180
actactatca ccacttcgac ccggccacca tccggtccaa ccaccaccac cagggctacc    240
tcaacaagct catcaactcc acccacgagc tctggggtcc gatttgccgg cgttaacatc    300
gcgggttttg actttggctg taccacagat ggcacttgcg ttacctcgaa ggtttatcct    360
ccgttgaaga acttcaccgg ctcaaacaac taccccgatg gcatcggcca gatgcagcac    420
ttcgtcaacg acgacgggat gactattttc cgcttacctg tcggatggca gtacctcgtc    480
aacaacaatt tgggcggcaa tcttgattcc acgagcattt ccaagtatga tcagcttgtt    540
caggggtgcc tgtctctggg cgcatactgc atcgtcgaca tccacaatta tgctcgatgg    600
aacggtggga tcattggtca gggcggccct actaatgctc aattcacgag cctttggtcg    660
cagttggcat caaagtacgc atctcagtcg agggtgtggt tcggcatcat gaatgagccc    720
cacgacgtga acatcaacac ctgggctgcc acggtccaag aggttgtaac cgcaatccgc    780
aacgctggtg ctacgtcgca attcatctct ttgcctggaa atgattggca atctgctggg    840
gctttcatat ccgatggcag tgcagccgcc ctgtctaaag tcacgaaccc ggatgggaca    900
atcacgaatc tgatttttga cgtgcacaaa tacttggact cagacaactc cggtactaat    960
cttgaatgtg tgacaaataa cattgacggc gccttttctc cgcttgccac ttggctccga   1020
cagaacaatc gccaggctat cctgacagaa accggtggtg gcaacgttca gtcctgcata   1080
caagacatgt gccagcaaat ccaatatctc aaccagaact cagatgtcta tcttggctat   1140
gttggttggg gtgccggatc atttgatagc acgtatgtcc tgacggaaac accgactggc   1200
agtggtaact catggacgga cacatccttg gtcagctcgt gtctagcaag aaagtag      1257
```

<210> SEQ ID NO 16
<211> LENGTH: 418
<212> TYPE: PRT
<213> ORGANISM: Artificial Sequence
<220> FEATURE:
<223> OTHER INFORMATION: 146C4

<400> SEQUENCE: 16

```
Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95
```

```
Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Lys Val Thr Asn Pro Asp Gly Thr Ile Thr Asn Leu
    290                 295                 300

Ile Phe Asp Val His Lys Tyr Leu Asp Ser Asp Asn Ser Gly Thr Asn
305                 310                 315                 320

Leu Glu Cys Val Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys
```

<210> SEQ ID NO 17
<211> LENGTH: 1257
<212> TYPE: DNA
<213> ORGANISM: Artificial Sequence
<220> FEATURE:
<223> OTHER INFORMATION: 149E4

<400> SEQUENCE: 17

```
atgaacaagt ccgtggctcc attgctgctt gcagcgtcca tactatatgg cggcgccgct      60

gcacagcaga ctgtctgggg ccagtgtgga ggtattggtt ggagcggacc tacgaattgt     120

gctcctggct cagcttgttc gaccctcaat ccttattatg cgcaatgtat tccgggagcc     180
```

```
actactatca ccacttcgac ccggccacca tccggtccaa ccaccaccac cagggctacc    240

tcaacaagct catcaactcc acccacgagc tctggggtcc gatttgccgg cgttaacatc    300

gcgggttttg actttggctg taccacagat ggcacttgcg ttacctcgaa ggtttatcct    360

ccgttgaaga acttcaccgg ctcaaacaac taccccgatg gcatcggcca gatgtcccac    420

ttcgtcaacg acgacgggat gactattttc cgcttacctg tcggatggca gtacctcgtc    480

aacaacaatt tgggcggcaa tcttgattcc acgagcattt ccaagtatga tcagcttgtt    540

caggggtgcc tgtctctggg cgcatactgc atcgtcgaca tccacaatta tgctcgatgg    600

aacggtggga tcattggtca gggcggccct actaatgctc aattcacgag cctttggtcg    660

cagttggcat caaagtacgc atctcagtcg agggtgtggt tcggcatcat gaatgagccc    720

cacgacgtga acatcaacac ctgggctgcc acggtccaag aggttgtaac cgcaatccgc    780

aacgctggtg ctacgtcgca attcatctct ttgcctggaa atgattggca atctgctggg    840

gctttcatat ccgatggcag tgcagccgcc ctgtctcaag tcacgaaccc ggatgggtca    900

acaacgaatc tgatttttga cgtgcacaaa tacttggact cagacaactc cggtactcac    960

gccgaatgtg taacaaataa cattgacgcc gcctttgcac cgcttgccac ttggctccga   1020

gcaaacggtc gccaggctat cctgagcgaa accggtggtg gcaacaccgc gtcctgccag   1080

acatatttgt gccagcaagt tgcttatctc aacgcaaact cagatgtcta tcttggctat   1140

attggttggt ctgccggatc atttgatagc acgtatgtcc tgacggaaac accgactggc   1200

agtggtaact catggacgga cacatccttg gtcagctcgt gtctagcaag aaagtag      1257
```

```
<210> SEQ ID NO 18
<211> LENGTH: 418
<212> TYPE: PRT
<213> ORGANISM: Artificial Sequence
<220> FEATURE:
<223> OTHER INFORMATION: 149E4

<400> SEQUENCE: 18

Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Ser His Phe Val Asn Asp
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175
```

```
Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Val Thr Asn Asn Ile Asp Ala Ala Phe Ala Pro Leu Ala
                325                 330                 335

Thr Trp Leu Arg Ala Asn Gly Arg Gln Ala Ile Leu Ser Glu Thr Gly
            340                 345                 350

Gly Gly Asn Thr Ala Ser Cys Gln Thr Tyr Leu Cys Gln Gln Val Ala
        355                 360                 365

Tyr Leu Asn Ala Asn Ser Asp Val Tyr Leu Gly Tyr Ile Gly Trp Ser
    370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys
```

<210> SEQ ID NO 19
<211> LENGTH: 1257
<212> TYPE: DNA
<213> ORGANISM: Artificial Sequence
<220> FEATURE:
<223> OTHER INFORMATION: 173C6

<400> SEQUENCE: 19

```
atgaacaagt ccgtggctcc attgctgctt gcagcgtcca tactatatgg cggcgccgct     60

gcacagcaga ctgtctgggg ccagtgtgga ggtattggtt ggagcggacc tacgaattgt    120

gctcctggct cagcttgttc gaccctcaat ccttattatg cgcaatgtat tccgggagcc    180

actactatca ccacttcgac ccggccacca tccggtccaa ccaccaccac cagggctacc    240

tcaacaagct catcaactcc acccacgagc tctggggtcc gatttgccgg cgttaacatc    300

gcgggttttg actttggctg taccacagat ggcacttgcg ttacctcgaa ggtttatcct    360

ccgttgaaga acttcaccgg ctcaaacaac taccccgatg gcatcggcca gatgcagcac    420

ttcgtcaacg acgacgggat gactattttc cgcttacctg tcggatggca gtacctcgtc    480

aacaacaatt tgggcggcaa tcttgattcc acgagcattt ccaagtatga tcagcttgtt    540

caggggtgcc tgtctctggg cgcatactgc atcgtcgaca tccacaatta tgctcgatgg    600

aacggtggga tcattggtca gggcggccct actaatgctc aattcacgag cctttggtcg    660
```

```
cagttggcat caaagtacgc atctcagtcg agggtgtggt tcggcatcat gaatgagccc    720

cacgacgtga acatcaacac ctgggctgcc acggtccaag aggttgtaac cgcaatccgc    780

aacgctggtg ctacgtcgca attcatctct ttgcctggaa atgattggca atctgctggg    840

gctttcatat ccgatggcag tgcagccgcc ctgtctcaag tcacgaaccc ggatgggtca    900

acaacgaatc tgatttttga cgtgcacaaa tacttggact cagacaactc cggtactcac    960

gccgaatgta ctacaaataa cattgacacc gcctttgcac cgcttgccac ttggctccga   1020

gcaaacggac gccaggctat cctgacagaa accggtggtg gcaacgttgc ttcctgcgag   1080

acatatttgt gccaggaagt tgcttatctc aacgccaact cagatgtcta tcttggctat   1140

gttggttggg gtgccggatc atttgatagc acgtatgtcc tgacggaaac accgactggc   1200

agtggtaact catggacgga cacatccttg gtcagctcgt gtctagcaag aaagtag      1257


<210> SEQ ID NO 20
<211> LENGTH: 418
<212> TYPE: PRT
<213> ORGANISM: Artificial Sequence
<220> FEATURE:
<223> OTHER INFORMATION: 173C6

<400> SEQUENCE: 20

Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
```

```
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Thr Ala Phe Ala Pro Leu Ala
                325                 330                 335

Thr Trp Leu Arg Ala Asn Gly Arg Gln Ala Ile Leu Thr Glu Thr Gly
            340                 345                 350

Gly Gly Asn Val Ala Ser Cys Glu Thr Tyr Leu Cys Gln Glu Val Ala
        355                 360                 365

Tyr Leu Asn Ala Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys


<210> SEQ ID NO 21
<211> LENGTH: 1257
<212> TYPE: DNA
<213> ORGANISM: Artificial Sequence
<220> FEATURE:
<223> OTHER INFORMATION: 191H11

<400> SEQUENCE: 21

atgaacaagt ccgtggctcc attgctgctt gcagcgtcca tactatatgg cggcgccgct     60

gcacagcaga ctgtctgggg ccagtgtgga ggtattggtt ggagcggacc tacgaattgt    120

gctcctggct cagcttgttc gaccctcaat ccttattatg cgcaatgtat tccgggagcc    180

actactatca ccacttcgac ccggccacca tccggtccaa ccaccaccac cagggctacc    240

tcaacaagct catcaactcc acccacgagc tctggggtcc gatttgccgg cgttaacatc    300

gcgggttttg actttggctg taccacagat ggcacttgcg ttacctcgaa ggtttatcct    360

ccgttgaaga acttcaccgg ctcaaacaac taccccgatg gcatcggcca gatgcagcac    420

ttcgtcaacg acgacgggat gactattttc cgcttacctg tcggatggca gtacctcgtc    480

aacaacaatt tgggcggcaa tcttgattcc acgagcattt ccaagtatga tcagcttgtt    540

caggggtgcc tgtctctggg cgcatactgc atcgtcgaca tccacaatta tgctcgatgg    600

aacggtggga tcattggtca gggcggccct actaatgctc aattcacgag cctttggtcg    660

cagttggcat caaagtacgc atctcagtcg agggtgtggt tcggcatcat gaatgagccc    720

cacgacgtga acatcaacac ctgggctgcc acggtccaag aggttgtaac cgcaatccgc    780

aacgctggtg ctacgtcgca attcatctct ttgcctggaa atgattggca atctgctggg    840

gctttcatat ccgatggcag tgcagccgcc ctgtctcaag tcacgaaccc ggatgggtca    900

acaacgaatc tgatttttga cgtgcacaaa tacttggact cagacaactc cggtactcac    960

gccgaatgta ctacaaataa cattgacgcc gcctttgcac cgcttgccac ttggctccga   1020

gcaaacggtc gccaggctat cctgagcgaa accggtggtg gcaacaccgc gtcctgccag   1080

acatatttgt gccagcaagt tgcttatctc aacgcaaact cagatgtcta tcttggctat   1140
```

```
attggttggt ctgccggatc atttgatagc acgtatgtcc tgacggaaac accgactggc   1200

agtggtaact catggacgga cacatccttg gtcagctcgt gtctagcaag aaagtag      1257


<210> SEQ ID NO 22
<211> LENGTH: 418
<212> TYPE: PRT
<213> ORGANISM: Artificial Sequence
<220> FEATURE:
<223> OTHER INFORMATION: 191H11

<400> SEQUENCE: 22

Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Ala Ala Phe Ala Pro Leu Ala
                325                 330                 335

Thr Trp Leu Arg Ala Asn Gly Arg Gln Ala Ile Leu Ser Glu Thr Gly
            340                 345                 350
```

```
Gly Gly Asn Thr Ala Ser Cys Gln Thr Tyr Leu Cys Gln Gln Val Ala
        355                 360                 365

Tyr Leu Asn Ala Asn Ser Asp Val Tyr Leu Gly Tyr Ile Gly Trp Ser
    370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys


<210> SEQ ID NO 23
<211> LENGTH: 1260
<212> TYPE: DNA
<213> ORGANISM: Artificial Sequence
<220> FEATURE:
<223> OTHER INFORMATION: 222E1

<400> SEQUENCE: 23

atgaacaagt ccgtggctcc attgctgctt gcagcgtcca tactatatgg cggcgccgct      60

gcacagcaga ctgtctgggg ccagtgtgga ggtattggtt ggagcggacc tacgaattgt     120

gctcctggct cagcttgttc gaccctcaat ccttattatg cgcaatgtat tccgggagcc     180

actactatca ccacttcgac ccggccacca tccggtccaa ccaccaccac cagggctacc     240

tcaacaagct catcaactcc acccacgagc tctggggtcc gatttgccgg cgttaacatc     300

gcgggttttg actttggctg taccacagat ggcacttgcg ttacctcgaa ggtttatcct     360

ccgttgaaga acttcaccgg ctcaaacaac taccccgatg gcatcggcca gatgcagcac     420

ttcgtcaacg acgacgggat gactattttc cgcttacctg tcggatggca gtacctcgtc     480

aacaacaatt tgggcggcaa tcttgattcc acgagcattt ccaagtatga tcagcttgtt     540

caggggtgcc tgtctctggg cgcatactgc atcgtcgaca tccacaatta tgctcgatgg     600

aacggtggga tcattggtca gggcggccct actaatgctc aattcacgag cctttggtcg     660

cagttggcat caaagtacgc atctcagtcg agggtgtggt tcggcatcat gaatgagccc     720

cacgacgtga acatcaacac ctgggctgcc acggtccaag aggttgtaac cgcaatccgc     780

aacgctggtg ctacgtcgca attcatctct ttgcctggaa atgattggca atctgctggg     840

gctttcatat ccgatggcag tgcagccgcc ctgtctcaag tcacgaaccc ggatgggtca     900

acaacgaatc tgatttttga cgtgcacaaa tacttggact cagacaactc cggtactcac     960

gccgaatgtg taacaaataa cattgacgcc gcctttgcac cgcttgccac ttggctccga    1020

gcaaacggac gccaggctat cctgacagaa accggtggtg gcaacgttgc ttcctgcgag    1080

acatatttgt gccaggaagt tgcttatctc aacgcaaact cagatgtcta tcttggctat    1140

gttggttggg ctgccggatc atttgatacg aattatacac tgacggaaac accgaatggc    1200

agtggttcat caatgacgga ccaaccattg gtcgcggctt gtctaactag atcgaattag    1260


<210> SEQ ID NO 24
<211> LENGTH: 419
<212> TYPE: PRT
<213> ORGANISM: Artificial Sequence
<220> FEATURE:
<223> OTHER INFORMATION: 222E1

<400> SEQUENCE: 24

Met Asn Lys Ser Val Ala Pro Leu Leu Leu Ala Ala Ser Ile Leu Tyr
1               5                   10                  15
```

```
Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Val Thr Asn Asn Ile Asp Ala Ala Phe Ala Pro Leu Ala
                325                 330                 335

Thr Trp Leu Arg Ala Asn Gly Arg Gln Ala Ile Leu Thr Glu Thr Gly
            340                 345                 350

Gly Gly Asn Val Ala Ser Cys Glu Thr Tyr Leu Cys Gln Glu Val Ala
        355                 360                 365

Tyr Leu Asn Ala Asn Ser Asp Val Tyr Leu Gly Tyr Val Gly Trp Ala
    370                 375                 380

Ala Gly Ser Phe Asp Thr Asn Tyr Thr Leu Thr Glu Thr Pro Asn Gly
385                 390                 395                 400

Ser Gly Ser Ser Met Thr Asp Gln Pro Leu Val Ala Ala Cys Leu Thr
                405                 410                 415

Arg Ser Asn
```

<210> SEQ ID NO 25
<211> LENGTH: 1260
<212> TYPE: DNA
<213> ORGANISM: Artificial Sequence
<220> FEATURE:
<223> OTHER INFORMATION: 225C7

<400> SEQUENCE: 25

```
atgaacaagt ccgtggctcc attgctgctt gcagcgtcca tactatatgg cggcgccgct     60

gcacagcaga ctgtctgggg ccagtgtgga ggtattggtt ggagcggacc tacgaattgt    120

gctcctggct cagcttgttc gaccctcaat ccttattatg cgcaatgtat tccgggagcc    180

actactatca ccacttcgac ccggccacca tccggtccaa ccaccaccac cagggctacc    240

tcaacaagct catcaactcc acccacgagc tctggggtcc gatttgccgg cgttaacatc    300

gcgggttttg actttggctg taccacagat ggcacttgcg ttacctcgaa ggtttatcct    360

ccgttgaaga acttcaccgg ctcaaacaac taccccgatg gcctcggcca gatgtcccac    420

ttcgtcaaaa gcacagggca caatattttc cgcttacctg tcggatggca gtacctcgtc    480

aacaacgttt tgggcggcac acttgattcc aacaatttcg caacctatga ttcacttgtt    540

caggggtgcc tggcaacagg cgcaagttgc atcattgaca tccacaatta tgctcgatgg    600

aacggtggga tcattggtca gggcggccct actaatgctc aattcacgag cctttggtcg    660

cagttggcat caaagtacgc atctcagtcg agggtgtggt tcggcatcat gaatgagccc    720

cacgacgtga acatcaacac ctgggctgcc acggtccaag aggttgtaac cgcaatccgc    780

aacgctggtg ctacgtcgca attcatctct ttgcctggaa atgattggca atctgctggg    840

gctttcatat ccgatggcag tgcagccgcc ctgtctcaag tcacgaaccc ggatgggtca    900

acaacgaatc tgatttttga cgtgcacaaa tacttggact cagacaactc cggtactcac    960

gccgaatgta ctacaaataa cattgacggc gccttttctc cgcttgccac ttggctccga   1020

gcaaacggac gccaggctat cctgagcgaa accggtggtg gcaacaccgc gtcctgccag   1080

acatatttgt gccagcaagt tgcttatctc aacgcaaact cagatgtcta tcttggctat   1140

attggttggt ctgccggatc atttgatagc acgtatattc tgacggaaac accgaatggc   1200

agtggttctt caatgacgga ccaagcgttg gtcgcggctt gtctaactag aacatcgtag   1260
```

<210> SEQ ID NO 26
<211> LENGTH: 419
<212> TYPE: PRT
<213> ORGANISM: Artificial Sequence
<220> FEATURE:
<223> OTHER INFORMATION: 225C7

<400> SEQUENCE: 26

```
Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95
```

```
Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Leu Gly Gln Met Ser His Phe Val Lys Ser
    130                 135                 140

Thr Gly His Asn Ile Phe Arg Leu Pro Val Gly Trp Gln Tyr Leu Val
145                 150                 155                 160

Asn Asn Val Leu Gly Gly Thr Leu Asp Ser Asn Asn Phe Ala Thr Tyr
                165                 170                 175

Asp Ser Leu Val Gln Gly Cys Leu Ala Thr Gly Ala Ser Cys Ile Ile
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Ala Asn Gly Arg Gln Ala Ile Leu Ser Glu Thr Gly
            340                 345                 350

Gly Gly Asn Thr Ala Ser Cys Gln Thr Tyr Leu Cys Gln Gln Val Ala
        355                 360                 365

Tyr Leu Asn Ala Asn Ser Asp Val Tyr Leu Gly Tyr Ile Gly Trp Ser
    370                 375                 380

Ala Gly Ser Phe Asp Ser Thr Tyr Ile Leu Thr Glu Thr Pro Asn Gly
385                 390                 395                 400

Ser Gly Ser Ser Met Thr Asp Gln Ala Leu Val Ala Ala Cys Leu Thr
                405                 410                 415

Arg Thr Ser
```

<210> SEQ ID NO 27
<211> LENGTH: 1248
<212> TYPE: DNA
<213> ORGANISM: Artificial Sequence
<220> FEATURE:
<223> OTHER INFORMATION: 227C4

<400> SEQUENCE: 27

```
atgaacaagt ccgtggctcc attgctgctt gcagcgtcca tactatatgg cggcgccgct     60

gcacagcaga ctgtctgggg ccagtgtgga ggtattggtt ggagcggacc tacgaattgt    120

gctcctggct cagcttgttc gaccctcaat ccttattatg cgcaatgtat tccgggagcc    180

actactatca ccacttcgac ccggccacca tccggtccaa ccaccaccac cagggctacc    240
```

```
tcaacaagct catcaactcc acccacgagc tctggggtcc gatttgccgg cgttaacatc    300

gcgggttttg actttggctg taccacagat ggcacttgcc taaccaataa ggtttatcct    360

gctttgagtt ccctcaacaa cggccccgat ggcctgggcc agatggccca cttcgtctcc    420

aaaactgggc ataatatttt ccgcttacct gtcggatggc agtacctcgt caacaacaat    480

ttgggcggca cacttgattc ctccaacctt gcgacctatg atttgcttgt tcaggggtgc    540

ctgtctctgg gcgcatactg catcgtcgac atccacaatt atgctcgatg gaacggtggg    600

atcattggtc agggcggccc tactaatgct caattcacga gcctttggtc gcagttggca    660

tcaaagtacg catctcagtc gagggtgtgg ttcggcatca tgaatgagcc ccacgacgtg    720

aacatcaaca cctgggctgc cacggtccaa gaggttgtaa ccgcaatccg caacgctggt    780

gctacgtcgc aattcatctc tttgcctgga aatgattggc aatctgctgg ggctttcata    840

tccgatggca gtgcagccgc cctgtctcaa gtcacgaacc cggatgggtc aacaacgaat    900

ctgatttttg acgtgcacaa atacttggac tcagacaact ccggtactca cgccgaatgt    960

gtaacaaata acattgacgc cgcctttgca ccgcttgcca cttggctccg agcaaacggt   1020

cgccaggcta tcctgacaga aaccggtggt ggcaacgttc agtcctgcat acaagacatg   1080

tgccagcaaa tccaatatct caaccagaac tcagatgtct atcttggcta tgttggttgg   1140

ggtgccggat catttgatag cacgtatgtc ctgacggaaa caccgactgg cagtggtaac   1200

tcatggacgg acacatcctt ggtcagctcg tgtctagcaa gaaagtag                1248
```

<210> SEQ ID NO 28
<211> LENGTH: 415
<212> TYPE: PRT
<213> ORGANISM: Artificial Sequence
<220> FEATURE:
<223> OTHER INFORMATION: 227C4

<400> SEQUENCE: 28

```
Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Leu Thr Asn Lys Val Tyr Pro Ala Leu Ser Ser Leu Asn Asn Gly
        115                 120                 125

Pro Asp Gly Leu Gly Gln Met Ala His Phe Val Ser Lys Thr Gly His
    130                 135                 140

Asn Ile Phe Arg Leu Pro Val Gly Trp Gln Tyr Leu Val Asn Asn Asn
145                 150                 155                 160

Leu Gly Gly Thr Leu Asp Ser Ser Asn Leu Ala Thr Tyr Asp Leu Leu
                165                 170                 175

Val Gln Gly Cys Leu Ser Leu Gly Ala Tyr Cys Ile Val Asp Ile His
```

```
            180                 185                 190

Asn Tyr Ala Arg Trp Asn Gly Gly Ile Ile Gly Gln Gly Gly Pro Thr
        195                 200                 205

Asn Ala Gln Phe Thr Ser Leu Trp Ser Gln Leu Ala Ser Lys Tyr Ala
    210                 215                 220

Ser Gln Ser Arg Val Trp Phe Gly Ile Met Asn Glu Pro His Asp Val
225                 230                 235                 240

Asn Ile Asn Thr Trp Ala Ala Thr Val Gln Glu Val Val Thr Ala Ile
                245                 250                 255

Arg Asn Ala Gly Ala Thr Ser Gln Phe Ile Ser Leu Pro Gly Asn Asp
            260                 265                 270

Trp Gln Ser Ala Gly Ala Phe Ile Ser Asp Gly Ser Ala Ala Ala Leu
        275                 280                 285

Ser Gln Val Thr Asn Pro Asp Gly Ser Thr Thr Asn Leu Ile Phe Asp
    290                 295                 300

Val His Lys Tyr Leu Asp Ser Asp Asn Ser Gly Thr His Ala Glu Cys
305                 310                 315                 320

Val Thr Asn Asn Ile Asp Ala Ala Phe Ala Pro Leu Ala Thr Trp Leu
                325                 330                 335

Arg Ala Asn Gly Arg Gln Ala Ile Leu Thr Glu Thr Gly Gly Gly Asn
            340                 345                 350

Val Gln Ser Cys Ile Gln Asp Met Cys Gln Gln Ile Gln Tyr Leu Asn
        355                 360                 365

Gln Asn Ser Asp Val Tyr Leu Gly Tyr Val Gly Trp Gly Ala Gly Ser
    370                 375                 380

Phe Asp Ser Thr Tyr Val Leu Thr Glu Thr Pro Thr Gly Ser Gly Asn
385                 390                 395                 400

Ser Trp Thr Asp Thr Ser Leu Val Ser Ser Cys Leu Ala Arg Lys
                405                 410                 415
```

<210> SEQ ID NO 29
<211> LENGTH: 1257
<212> TYPE: DNA
<213> ORGANISM: Artificial Sequence
<220> FEATURE:
<223> OTHER INFORMATION: 229D1

<400> SEQUENCE: 29

```
atgaacaagt ccgtggctcc attgctgctt gcagcgtcca tactatatgg cggcgccgct     60

gcacagcaga ctgtctgggg ccagtgtgga ggtattggtt ggagcggacc tacgaattgt    120

gctcctggct cagcttgttc gaccctcaat ccttattatg cgcaatgtat tccgggagcc    180

actactatca ccacttcgac ccggccacca tccggtccaa ccaccaccac cagggctacc    240

tcaacaagct catcaactcc acccacgagc tctggggtcc gatttgccgg cgttaacatc    300

gcgggttttg actttggctg taccacagat ggcacttgcg ttacctcgaa ggtttatcct    360

ccgttgaaga acttcaccgg ctcaaacaac taccccgatg gcatcggcca gatgcagcac    420

ttcgtcaacg acgacgggat gactattttc cgcttacctg tcggatggca gtacctcgtc    480

aacaacaatt tgggcggcaa tcttgattcc acgagcattt ccaagtatga tcagcttgtt    540

caggggtgcc tgtctctggg cgcatactgc atcgtcgaca tccacaatta tgctcgatgg    600

aacggtggga tcattggtca gggcggccct actaatgctc aattcacgag cctttggtcg    660

cagttggcat caaagtacgc atctcagtcg agggtgtggt tcggcatcat gaatgagccc    720

cacgacgtga acatcaacac ctgggctgcc acggtccaag aggttgtaac cgcaatccgc    780
```

```
aacgctggtg ctacgtcgca attcatctct ttgcctggaa atgattggca atctgctggg    840

gctttcatat ccgatggcag tgcagccgcc ctgtctcaag tcacgaaccc ggatgggtca    900

acaacgaatc tgatttttga cgtgcacaaa tacttggact cagacaactc cggtactcac    960

gccgaatgta ctacaaataa cattgacggc gccttttctc cgcttgccac ttggctccga   1020

cagaacaatc gccaggctat cctgacagaa accggtggtg gcaacaccgc gtcctgccag   1080

acatatttgt gccagcaagt tgcttatctc aacgcaaact cagatgtcta tcttggctat   1140

attggttggt ctgccggatc atttgatagc acgtatattc tgacggaaac accgactggc   1200

agtggtaact catggacgga cacatccttg gtcagctcgt gtctagcaag aaagtag      1257
```

```
<210> SEQ ID NO 30
<211> LENGTH: 418
<212> TYPE: PRT
<213> ORGANISM: Artificial Sequence
<220> FEATURE:
<223> OTHER INFORMATION: 229D1

<400> SEQUENCE: 30

Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
```

```
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Thr Ala Ser Cys Gln Thr Tyr Leu Cys Gln Gln Val Ala
        355                 360                 365

Tyr Leu Asn Ala Asn Ser Asp Val Tyr Leu Gly Tyr Ile Gly Trp Ser
    370                 375                 380

Ala Gly Ser Phe Asp Ser Thr Tyr Ile Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys


<210> SEQ ID NO 31
<211> LENGTH: 1257
<212> TYPE: DNA
<213> ORGANISM: Artificial Sequence
<220> FEATURE:
<223> OTHER INFORMATION: 231C9

<400> SEQUENCE: 31

atgaacaagt ccgtggctcc attgctgctt gcagcgtcca tactatatgg cggcgccgct      60

gcacagcaga ctgtctgggg ccagtgtgga ggtattggtt ggagcggacc tacgaattgt     120

gctcctggct cagcttgttc gaccctcaat ccttattatg cgcaatgtat tccgggagcc     180

actactatca ccacttcgac ccggccacca tccggtccaa ccaccaccac cagggctacc     240

tcaacaagct catcaactcc acccacgagc tctggggtcc gatttgccgg cgttaacatc     300

gcgggttttg actttggctg taccacagat ggcacttgcg ttacctcgaa ggtttatcct     360

ccgttgaaga acttcaccgg ctcaaacaac taccccgatg gcatcggcca gatgcagcac     420

ttcgtcaacg acgacgggat gactattttc cgcttacctg tcggatggca gtacctcgtc     480

aacaacaatt tgggcggcaa tcttgattcc acgagcattt ccaagtatga tcagcttgtt     540

caggggtgcc tgtctctggg cgcatactgc atcgtcgaca tccacaatta tgctcgatgg     600

aacggtggga tcattggtca gggcggccct actaatgctc aattcacgag cctttggtcg     660

cagttggcat caaagtacgc atctcagtcg agggtgtggt tcggcatcat gaatgagccc     720

cacgacgtga acatcaacac ctgggctgcc acggtccaag aggttgtaac cgcaatccgc     780

aacgctggtg ctacgtcgca attcatctct ttgcctggaa atgattggca atctgctggg     840

gctttcatat ccgatggcag tgcagccgcc ctgtctcaag tcacgaaccc ggatgggtca     900

acaacgaatc tgatttttga cgtgcacaaa tacttggact cagacaactc cggtactcac     960

gccgaatgtg taacaaataa cattgacgcc gcctttgcac cgcttgccac ttggctccga    1020

gcaaacggtc gccaggctat cctgagcgaa accggtggtg gcaacaccgc gtcctgccag    1080

acatatttgt gccagcaagt tgcttatctc aacgcaaact cagatgtcta tcttggctat    1140

attggttggg gtgccggatc atttgatagc acgtatgtcc tgacggaaac accgactggc    1200

agtggtaact catggacgga cacatccttg gtcagctcgt gtctagcaag aaagtag       1257
```

<210> SEQ ID NO 32
<211> LENGTH: 418
<212> TYPE: PRT
<213> ORGANISM: Artificial Sequence
<220> FEATURE:
<223> OTHER INFORMATION: 231C9

<400> SEQUENCE: 32

```
Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Val Thr Asn Asn Ile Asp Ala Ala Phe Ala Pro Leu Ala
                325                 330                 335

Thr Trp Leu Arg Ala Asn Gly Arg Gln Ala Ile Leu Ser Glu Thr Gly
            340                 345                 350

Gly Gly Asn Thr Ala Ser Cys Gln Thr Tyr Leu Cys Gln Gln Val Ala
        355                 360                 365
```

```
Tyr Leu Asn Ala Asn Ser Asp Val Tyr Leu Gly Tyr Ile Gly Trp Gly
    370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys


<210> SEQ ID NO 33
<211> LENGTH: 1260
<212> TYPE: DNA
<213> ORGANISM: Artificial Sequence
<220> FEATURE:
<223> OTHER INFORMATION: 330F9

<400> SEQUENCE: 33

atgaacaagt ccgtggctcc attgctgctt gcagcgtcca tactatatgg cggcgccgct     60

gcacagcaga ctgtctgggg ccagtgtgga ggtattggtt ggagcggacc tacgaattgt    120

gctcctggct cagcttgttc gaccctcaat ccttattatg cgcaatgtat tccgggagcc    180

actactatca ccacttcgac ccggccacca tccggtccaa ccaccaccac cagggctacc    240

tcaacaagct catcaactcc acccacgagc tctggggtcc gatttgccgg cgttaacatc    300

gcgggttttg actttggctg taccacagat ggcacttgcg ttacctcgaa ggtttatcct    360

ccgttgaaga acttcaccgg ctcaaacaac taccccgatg gcatcggcca gatgcagcac    420

ttcgtcaacg acgacgggat gactattttc cgcttacctg tcggatggca gtacctcgtc    480

aacaacaatt tgggcggcaa tcttgattcc acgagcattt ccaagtatga tcagcttgtt    540

caggggtgcc tgtctctggg cgcatactgc atcgtcgaca tccacaatta tgctcgatgg    600

aacggtggga tcattggtca gggcggccct actaatgctc aattcacgag cctttggtcg    660

cagttggcat caaagtacgc atctcagtcg agggtgtggt tcggcatcat gaatgagccc    720

cacgacgtga acatcaacac ctgggctgcc acggtccaag aggttgtaac cgcaatccgc    780

aacgctggtg ctacgtcgca attcatctct ttgcctggaa atgattggca atctgctggg    840

gctttcatat ccgatggcag tgcagccgcc ctgtctcaag tcacgaaccc ggatgggtca    900

acaacgaatc tgatttttga cgtgcacaaa tacttggact cagacaactc cggtactcac    960

gccgaatgtg taacaaataa cattgacgcc gcctttgcac cgcttgccac ttggctccga   1020

gcaaacggtc gccaggctat cctgagcgaa accggtggtg gcaacaccgc gtcctgccag   1080

acatatttgt gccagcaagt tgcttatctc aacgcaaact cagatgtcta tcttggctat   1140

gttggttggg ctgccggatc atttgatacg aattatacac tgacggaaac accgaatggc   1200

agtggttctt caatgacgga ccaagcgttg gtcgcggctt gtctaactag atcgaattag   1260


<210> SEQ ID NO 34
<211> LENGTH: 419
<212> TYPE: PRT
<213> ORGANISM: Artificial Sequence
<220> FEATURE:
<223> OTHER INFORMATION: 330F9

<400> SEQUENCE: 34

Met Asn Lys Ser Val Ala Pro Leu Leu Leu Ala Ala Ser Ile Leu Tyr
1               5                   10                  15

Gly Gly Ala Ala Ala Gln Gln Thr Val Trp Gly Gln Cys Gly Gly Ile
            20                  25                  30
```

```
Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Ala Glu Cys Val Thr Asn Asn Ile Asp Ala Ala Phe Ala Pro Leu Ala
                325                 330                 335

Thr Trp Leu Arg Ala Asn Gly Arg Gln Ala Ile Leu Ser Glu Thr Gly
            340                 345                 350

Gly Gly Asn Thr Ala Ser Cys Gln Thr Tyr Leu Cys Gln Gln Val Ala
        355                 360                 365

Tyr Leu Asn Ala Asn Ser Asp Val Tyr Leu Gly Tyr Val Gly Trp Ala
    370                 375                 380

Ala Gly Ser Phe Asp Thr Asn Tyr Thr Leu Thr Glu Thr Pro Asn Gly
385                 390                 395                 400

Ser Gly Ser Ser Met Thr Asp Gln Ala Leu Val Ala Ala Cys Leu Thr
                405                 410                 415

Arg Ser Asn
```

<210> SEQ ID NO 35
<211> LENGTH: 1236
<212> TYPE: DNA

<213> ORGANISM: Botryotinia fuckeliana

<400> SEQUENCE: 35

```
atgaagctct ccaccaccgt atacacagtt gttcctttcc tgtctaccgc caccgcacag     60
ggcgttgctt acgcacagtg tggaggtaat ggttggactg gatctacggc ttgtgtgtca    120
ggctatgctt gttcgtatgt gaatgcgtat tattcgcaat gtttgccggg aactgcaact    180
ttaaccactg ttaccagtgc aaccaccagt gctagttcga aaacaagcac agccgcagca    240
cccaatagca cggggaagac aaaatatatc ggcaccaaca tcgcgggttt tgactttggc    300
tgtaccacag atggcacttg cctaaccaat aaggtttatc ctgctttgag ttccctcaac    360
aacggccccg atggcctggg ccagatggcc cacttcgtct ccaaaactgg gcataatatt    420
ttccgcttac ctgtcggatg gcagtacctc gtcaacaaca atttgggcgg cacacttgat    480
tcctccaacc ttgcgaccta tgatttgctt gttcaggggt gcctggcaac gggcgcaact    540
tgcgtgattg acatccacaa ttatgctcga tggaacggtg caatcattgg tcagggcggc    600
cctactgatg ctcaattcgc tagcctttgg tcgcagttgg caacgaagta caagtctaat    660
acgaaggtgg tcttcggctt gatgaatgag ccccacgact tgaacagcat caccacctgg    720
gctgccacgc ttcaaacagt tgtaaccgca atccgccagg ctggtgctac gtcgaccatg    780
cttctattgc ctggaagtga ttacacatct gctggggctt tcataaccga tggcagtgca    840
gccgccctgt ctaagatcac gaacctcgat gggactacaa cgaatctgat tttgacgtg     900
cacaaatact tggactcaga caactccggt actcacgccg aatgtgtaac aaataacatt    960
gacgccgcct ttgcaccgct tgccacttgg ctccgagcaa acggtcgcca ggctatcctg   1020
agcgaaaccg gtggtggcaa caccgcgtcc tgccagacat atttgtgcca gcaagttgct   1080
tatctcaacg caaactcaga tgtctatctt ggctatattg gttggtctgc cggatcattt   1140
gatagcacgt atattctgac ggaaacaccg aatggcagtg gttcttcaat gacggaccaa   1200
gcgttggtcg cggcttgtct aactagaaca tcgtag                             1236
```

<210> SEQ ID NO 36
<211> LENGTH: 411
<212> TYPE: PRT
<213> ORGANISM: Botryotinia fuckeliana

<400> SEQUENCE: 36

```
Met Lys Leu Ser Thr Thr Val Tyr Thr Val Val Pro Phe Leu Ser Thr
1               5                   10                  15

Ala Thr Ala Gln Gly Val Ala Tyr Ala Gln Cys Gly Gly Asn Gly Trp
            20                  25                  30

Thr Gly Ser Thr Ala Cys Val Ser Gly Tyr Ala Cys Ser Tyr Val Asn
        35                  40                  45

Ala Tyr Tyr Ser Gln Cys Leu Pro Gly Thr Ala Thr Leu Thr Thr Val
    50                  55                  60

Thr Ser Ala Thr Thr Ser Ala Ser Ser Lys Thr Ser Thr Ala Ala Ala
65                  70                  75                  80

Pro Asn Ser Thr Gly Lys Thr Lys Tyr Ile Gly Thr Asn Ile Ala Gly
                85                  90                  95

Phe Asp Phe Gly Cys Thr Thr Asp Gly Thr Cys Leu Thr Asn Lys Val
            100                 105                 110

Tyr Pro Ala Leu Ser Ser Leu Asn Asn Gly Pro Asp Gly Leu Gly Gln
        115                 120                 125

Met Ala His Phe Val Ser Lys Thr Gly His Asn Ile Phe Arg Leu Pro
```

```
    130                 135                 140

Val Gly Trp Gln Tyr Leu Val Asn Asn Asn Leu Gly Gly Thr Leu Asp
145                 150                 155                 160

Ser Ser Asn Leu Ala Thr Tyr Asp Leu Leu Val Gln Gly Cys Leu Ala
                165                 170                 175

Thr Gly Ala Thr Cys Val Ile Asp Ile His Asn Tyr Ala Arg Trp Asn
            180                 185                 190

Gly Ala Ile Ile Gly Gln Gly Gly Pro Thr Asp Ala Gln Phe Ala Ser
        195                 200                 205

Leu Trp Ser Gln Leu Ala Thr Lys Tyr Lys Ser Asn Thr Lys Val Val
    210                 215                 220

Phe Gly Leu Met Asn Glu Pro His Asp Leu Asn Ser Ile Thr Thr Trp
225                 230                 235                 240

Ala Ala Thr Leu Gln Thr Val Val Thr Ala Ile Arg Gln Ala Gly Ala
                245                 250                 255

Thr Ser Thr Met Leu Leu Leu Pro Gly Ser Asp Tyr Thr Ser Ala Gly
            260                 265                 270

Ala Phe Ile Thr Asp Gly Ser Ala Ala Ala Leu Ser Lys Ile Thr Asn
        275                 280                 285

Leu Asp Gly Thr Thr Thr Asn Leu Ile Phe Asp Val His Lys Tyr Leu
    290                 295                 300

Asp Ser Asp Asn Ser Gly Thr His Ala Glu Cys Val Thr Asn Asn Ile
305                 310                 315                 320

Asp Ala Ala Phe Ala Pro Leu Ala Thr Trp Leu Arg Ala Asn Gly Arg
                325                 330                 335

Gln Ala Ile Leu Ser Glu Thr Gly Gly Gly Asn Thr Ala Ser Cys Gln
            340                 345                 350

Thr Tyr Leu Cys Gln Gln Val Ala Tyr Leu Asn Ala Asn Ser Asp Val
        355                 360                 365

Tyr Leu Gly Tyr Ile Gly Trp Ser Ala Gly Ser Phe Asp Ser Thr Tyr
    370                 375                 380

Ile Leu Thr Glu Thr Pro Asn Gly Ser Gly Ser Ser Met Thr Asp Gln
385                 390                 395                 400

Ala Leu Val Ala Ala Cys Leu Thr Arg Thr Ser
                405                 410


<210> SEQ ID NO 37
<211> LENGTH: 1242
<212> TYPE: DNA
<213> ORGANISM: Sclerotinia sclerotiorum

<400> SEQUENCE: 37

atgaaggtgc caactcctct gtacactatc cttccgctag tatccagcgc cacagcacag     60

ggcgctgcct atgcacagtg tggaggtaaa ggttggacgg gagcaacgac ttgtgttgga    120

ggctatgtgt gtacttattc gagtgaatat tattcgcaat gtttaccggg aactgcgact    180

ctaaccactg ttaccagttc gtccaaacca tcaagctcta gtaccaagac ctcatcaagc    240

gcagcttcaa gctcaacggg aaaaacgaaa tatattggca ccaacatcgc gggttttgac    300

tttggctgta ccacagatgg cacttgcata acctcggaga tctatcctcc gttgagcagc    360

atagccaacc atcccgatgg cctcggccag atgtcccact tcgtcaaaag cacagggcac    420

aatattttcc gcttacctgt cggatggcag tacctcgtca acaacgtttt gggcggcaca    480

cttgattcca acaatttcgc aacctatgat tcacttgttc aggggtgcct ggcaacaggc    540
```

```
gcaagttgca tcattgacat ccacaattat gctcgatgga acggtgggat cattggtcag    600

ggcggcccta ctaatgctca attcgtgagc ctttggactc agttggcaaa taagtacaag    660

gggaatgcga aggtgatttt cggcttgatg aatgagcccc acgacatgcc aaacatcacc    720

acctgggctg cctcagtcca agcagttgta accgcaatcc gccaagctgg tgctacgtcg    780

accacgcttc tcttgcctgg aaatgattac acctctgctg ggtctttcat atccgatggc    840

agtgcagccg ccctgtctaa agtcacgaac ccggatggga caatcacgaa tctgattttt    900

gacgtgcaca aatacttgga ctcagacaac tccggtacta atcttgaatg tgtgacaaat    960

aacattgaca ccgcctttgc accgcttgcc acttggctcc gagcaaacgg acgccaggct   1020

atcctgacag aaaccggtgg tggcaacgtt gcttcctgcg agacatattt gtgccaggaa   1080

gttgcttatc tcaacgccaa ctcagatgtc tatcttggct atgttggttg ggctgccgga   1140

tcatttgata cgaattatac actgacggaa acaccgaatg gcagtggttc atcaatgacg   1200

gaccaaccat tggtcgcggc ttgtctaact agatcgaatt ag                      1242
```

<210> SEQ ID NO 38
<211> LENGTH: 413
<212> TYPE: PRT
<213> ORGANISM: Sclerotinia sclerotiorum

<400> SEQUENCE: 38

```
Met Lys Val Pro Thr Pro Leu Tyr Thr Ile Leu Pro Leu Val Ser Ser
1               5                   10                  15

Ala Thr Ala Gln Gly Ala Ala Tyr Ala Gln Cys Gly Gly Lys Gly Trp
            20                  25                  30

Thr Gly Ala Thr Thr Cys Val Gly Gly Tyr Val Cys Thr Tyr Ser Ser
        35                  40                  45

Glu Tyr Tyr Ser Gln Cys Leu Pro Gly Thr Ala Thr Leu Thr Thr Val
    50                  55                  60

Thr Ser Ser Ser Lys Pro Ser Ser Ser Ser Thr Lys Thr Ser Ser Ser
65                  70                  75                  80

Ala Ala Ser Ser Ser Thr Gly Lys Thr Lys Tyr Ile Gly Thr Asn Ile
                85                  90                  95

Ala Gly Phe Asp Phe Gly Cys Thr Thr Asp Gly Thr Cys Ile Thr Ser
            100                 105                 110

Glu Ile Tyr Pro Pro Leu Ser Ser Ile Ala Asn His Pro Asp Gly Leu
        115                 120                 125

Gly Gln Met Ser His Phe Val Lys Ser Thr Gly His Asn Ile Phe Arg
    130                 135                 140

Leu Pro Val Gly Trp Gln Tyr Leu Val Asn Asn Val Leu Gly Gly Thr
145                 150                 155                 160

Leu Asp Ser Asn Asn Phe Ala Thr Tyr Asp Ser Leu Val Gln Gly Cys
                165                 170                 175

Leu Ala Thr Gly Ala Ser Cys Ile Ile Asp Ile His Asn Tyr Ala Arg
            180                 185                 190

Trp Asn Gly Gly Ile Ile Gly Gln Gly Gly Pro Thr Asn Ala Gln Phe
        195                 200                 205

Val Ser Leu Trp Thr Gln Leu Ala Asn Lys Tyr Lys Gly Asn Ala Lys
    210                 215                 220

Val Ile Phe Gly Leu Met Asn Glu Pro His Asp Met Pro Asn Ile Thr
225                 230                 235                 240

Thr Trp Ala Ala Ser Val Gln Ala Val Val Thr Ala Ile Arg Gln Ala
                245                 250                 255
```

-continued

```
Gly Ala Thr Ser Thr Thr Leu Leu Leu Pro Gly Asn Asp Tyr Thr Ser
            260                 265                 270

Ala Gly Ser Phe Ile Ser Asp Gly Ser Ala Ala Ala Leu Ser Lys Val
        275                 280                 285

Thr Asn Pro Asp Gly Thr Ile Thr Asn Leu Ile Phe Asp Val His Lys
    290                 295                 300

Tyr Leu Asp Ser Asp Asn Ser Gly Thr Asn Leu Glu Cys Val Thr Asn
305                 310                 315                 320

Asn Ile Asp Thr Ala Phe Ala Pro Leu Ala Thr Trp Leu Arg Ala Asn
                325                 330                 335

Gly Arg Gln Ala Ile Leu Thr Glu Thr Gly Gly Gly Asn Val Ala Ser
            340                 345                 350

Cys Glu Thr Tyr Leu Cys Gln Glu Val Ala Tyr Leu Asn Ala Asn Ser
        355                 360                 365

Asp Val Tyr Leu Gly Tyr Val Gly Trp Ala Ala Gly Ser Phe Asp Thr
    370                 375                 380

Asn Tyr Thr Leu Thr Glu Thr Pro Asn Gly Ser Gly Ser Ser Met Thr
385                 390                 395                 400

Asp Gln Pro Leu Val Ala Ala Cys Leu Thr Arg Ser Asn
                405                 410
```

ENDOGLUCANASE VARIANTS HAVING IMPROVED ACTIVITY, AND USES OF SAME

This application is a U.S. national phase of International Application No. PCT/FR2014/052985, filed Nov. 21, 2014, which claims priority from French Patent application no. FR1361511, filed Nov. 22, 2013, the disclosure of each of which is hereby incorporated by reference in its entirety.

The possibility of producing ethanol from cellulose has received a great deal of attention owing to the availability of large amounts of raw material and also the value of ethanol as a fuel. The cellulose-based natural raw materials for such a process are denoted "biomass". Many types of biomass, for example wood, agricultural residues, herbaceous crops and municipal solid waste, have been considered as potential raw materials for producing biofuel. These materials consist mainly of cellulose, hemicellulose and lignin.

Cellulose is a polymer consisting of glucose molecules linked by beta-1,4 bonds, which are very resistant to breakdown or to depolymerization. Once the cellulose has been converted to glucose, the latter is easily fermented to biofuel, for example ethanol, using a yeast.

The oldest methods studied for converting the cellulose to glucose are based on acid hydrolysis. This process can be carried out in the presence of concentrated or dilute acids. However, several drawbacks, such as poor recovery of the acid when concentrated acids are used and the low production of glucose in the case of the use of dilute acids, are detrimental to the economy of the acid hydrolysis process.

To overcome the drawbacks of the acid hydrolysis process, cellulose conversion processes have more recently related to enzymatic hydrolysis, using enzymes of cellulase type. This enzymatic hydrolysis of lignocellulosic biomass (for example, cellulose) has, however, the drawback of being an expensive industrial process. As a result, it is necessary to use increasingly effective cellulase-secreting microorganism strains. In this respect, many microorganisms comprise enzymes which hydrolyze cellulose, such as the fungi *Trichoderma, Aspergillus, Humicola* or *Fusarium* and also the bacteria such as *Thermomonospora, Bacillus, Cellulomonas* and *Streptomyces*. The enzymes secreted by these microorganisms have three types of activities that are useful in the conversion of cellulose to glucose and are divided up into three groups: endoglucanases, which randomly attack cellulose fibers internally, exoglucanases which will attack the ends of the fibers, releasing cellobiose, and β-glucosidases which will hydrolyze this cellobiose to glucose. Other classes of enzymes such as hemicellulases or the recently discovered polysaccharide monooxygenase enzyme class can also play a role in the efficiency of the hydrolysis.

There is a strong industrial interest in decreasing the cost of enzymatic hydrolysis, and this decrease involves the use of a reduced amount of enzymes and therefore cocktails of enzymes that are more effective. Consequently, several patent applications describe natural enzymes with capacities greater than those of *Trichoderma reesei* or variants that have been improved by genetic engineering. Mention may be made of patent applications US2010304464, WO 2010/066411 and WO 2013/029176 relating to exoglucanases, applications WO 2007/109441, WO 2012/149192 and WO 2010/076388 relating to endoglucanases, applications WO 2010/029259, WO 2010/135836 or WO 2010/022518 relating to β-glucosidases, or else applications WO12135659 and WO12149344 relating to polysaccharide monooxygenases.

Enzymes which hydrolyze lignocellulosic biomass are classified in the CAZy system (Cantarel, B. L., Coutinho, P. M., Rancurel, C., Bernard, T., Lombard, V., & Henrissat, B. (2009). The Carbohydrate-Active EnZymes database (CAZy): an expert resource for Glycogenomics. Nucleic acids research, 37, D233-8) on the basis of principally structural criteria. Endoglucanases can belong to the families GH 5, 6, 7, 8, 9, 12, 16, 18, 19, 26, 44, 45, 48, 51, 74 and 124.

In order for a hydrolysis of the lignocellulosic biomass to be effective and economically comfortable, the enzymatic mixture must comprise equilibrated proportions of diverse enzymatic activities (inter alia, but not exclusively, exoglucanases, endoglucanases, xylanases and β-glucosidases). By way of example, in the native mixtures of *Trichoderma reesei*, the presence of 60-70% of exoglucanases, 15-20% of endoglucanases, a few percentages of hemicellulases and approximately 5-10% of β-glucosidases are generally noted. This mixture is suitable for hydrolyzing the majority of pretreated substrates (for example such as wheat straw steam-exploded under acid conditions) with acceptable yields. In short, the increase in the endoglucanase activity must not take place to the detriment of the other enzymatic activities. The functional specificities of these enzymes are at the current time poorly understood. The *Trichoderma reesei* genome comprises at least 3 main enzymes, derived from families 7 (EG1, cel7b), 5 (EG2, cel5a) and 12 (EG3, cel12a). The EG1 and EG2 enzymes are the major endoglucanases and can represent up to 10-20% by weight of the complete cocktail of enzymes produced by *T. reesei*.

Endoglucanases (EC 3.2.1.4), the first enzymes to act on cellulose, are known to have a major role in hydrolysis by increasing the number of sites that exoglucanases can attack, while decreasing the degree of polymerization of the microfibrils attacked. Recent studies (Szijártá, N., Siika-aho, M., Sontag-Strohm, T., & Viikari, L. (2011). Liquefaction of hydrothermally pretreated wheat straw at high-solids content by purified *Trichoderma* enzymes. *Bioresource technology,* 102(2), 1968-74) emphasize their role in decreasing the viscosity of the biomass during the first hours of hydrolysis. This decrease in viscosity can have a very significant impact on the operating costs of the process.

The viscosity problem is exacerbated in the case of processes which necessitate recourse to a low temperature, such as simultaneous saccharification and fermentation (SSF), which involves both the enzymes which hydrolyze the biomass and the microorganism which converts the sugar monomers to ethanol.

The hydrolysis and the fermentation can be carried out according to various schemes. The most common consists of separate hydrolysis and fermentation (SHF). This method makes it possible to optimize each step by maintaining the optimal reaction conditions. This fermentation is carried out extemporaneously, at a temperature of between approximately 28° C. and approximately 30° C., while the hydrolysis generally takes place at a temperature of at least 45° C. However, in SHF, the sugars released at the end of the reaction are present at very high concentration and lead to inhibition of the enzymes, slowing down the efficiency of the process. In order to avoid these drawbacks, another type of process can be envisioned. In SSF, the two steps (hydrolysis and fermentation of the hexoses) are carried out simultaneously, preventing accumulation of the sugars at concentrations that are inhibitory for the enzymes. The investment costs are also reduced by virtue of the use of a single reactor. The degree of hydrolysis is higher following the absence of inhibition since the sugars released are used immediately for the fermentation to ethanol. In this method, the reactor temperature necessarily constitutes a compromise between the optimal temperatures for hydrolysis and for fermentation, typically between approximately 30° C. and approximately 35° C. However, at such a temperature, the activity of the cellulolytic enzymes is decreased by approximately 30%.

SSF also allows the expression of enzymes that break down cellulose in the organism fermenting the sugars, thereby making it possible to limit, or in an extreme case eliminate, recourse to enzymes produced during a separate step.

Consequently, the obtaining of enzymes which maintain an effective endoglucanase activity at the optimal temperatures for hydrolysis and for fermentation (i.e. between 30° C. and 50° C.) while at the same time keeping the proportion of all the enzymes of the mixture would be a significant gain for the process of converting lignocellulosic biomass to biofuel.

DESCRIPTION OF THE INVENTION

The inventors have developed a polypeptide having an improved endoglucanase activity, in particular compared with the endoglucanase activity of the wild-type EG2 protein of sequence SEQ ID NO: 2. EG2 corresponds to *Trichoderma reesei* endoglucanase 2.

With this perspective, the applicants have to their great credit found, after numerous research studies, an isolated or purified polypeptide having an improved endoglucanase activity compared with the endoglucanase activity of the wild-type EG2 protein (SEQ ID NO: 2).

According to the invention, the polypeptide is chosen from the group consisting of:

i) an amino acid sequence chosen from SEQ ID NO: 4, SEQ ID NO: 6, SEQ ID NO: 8, SEQ ID NO: 10, SEQ ID NO: 12; SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 and SEQ ID NO: 34;

ii) an amino acid sequence having a percentage identity of at least 70%, preferentially of 75%, 80%, 85%, 90%, 95%, 98% or 99%, relative to the sequence SEQ ID NO: 4, SEQ ID NO: 6, SEQ ID NO: 8, SEQ ID NO: 10, SEQ ID NO: 12; SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 or SEQ ID NO: 34.

According to the invention, the percentage identity of a given sequence relative to SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 or SEQ ID NO: 34 corresponds to the number of residues that are identical between this given sequence and SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 or SEQ ID NO: 34 divided by the number of residues in SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 or SEQ ID NO: 34. When the GenomeQuest database is used, said percentage identity relative to SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 or SEQ ID NO: 34 corresponds to the Query percentage identity (% id Query), where Query corresponds to the sequence SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 or SEQ ID NO: 34.

In another embodiment, the polypeptide as described above is characterized in that its expression in a fermentative organism is at least equal to the expression of the wild-type EG2 protein (SEQ ID NO: 2).

Those skilled in the art will be able, for example, to determine the increase or in other words the improvement in the enzymatic activity either using the substrate carboxymethylcellulose (CMC), or with a chromogenic substrate (p-nitrophenyl glycoside). The enzymatic activity will be respectively revealed by colorimetric assay of the reducing sugars or else of the nitrophenol released.

Preferably, the polypeptide of the invention has an enzymatic activity improved by at least 10%, preferentially by at least 20%, preferentially by at least 30%, relative to the endoglucanase activity of the EG2 protein of amino acid sequence SEQ ID NO: 2.

An example of a protocol, that those skilled in the art will be able to use to determine whether a polypeptide according to the invention has an improved enzymatic activity relative to that of the wild-type EG2 protein (SEQ ID NO: 2) is the following:

- formation of a stock culture of *E. coli* expressing a polypeptide according to the invention overnight at 37° C.;
- inoculation of an LB culture medium with 1% of stock culture at 37° C. until an optical density of 0.4 is obtained;
- culture of said cells at 20° C. for 18 h;
- centrifugation for 5 minutes at 7900 rpm;
- resuspension of the cell pellets with 100 mM citrate phosphate buffer at pH 5 containing 1 mg/ml of lysozyme (final $OD_{600}$ 100);
- incubation of the resuspended cells for 30 minutes on ice;
- lysis of the cells by means of 3 cycles of freezing/thawing;
- fractionation of the DNA by sonication;
- centrifugation for 30 minutes at 13000 rpm;
- incubation of 100 μl of breaking supernatant diluted 50 times with 100 μl of 100 mM citrate phosphate buffer at pH 5 containing 1% of CMC for 1 h at 35 and 50° C.;
- removal of 100 μl of reaction;
- addition of 100 μl of DNS reagent (Miller, 1959);
- incubation for 5 minutes at 100° C.;
- incubation for 3 minutes on ice;
- centrifugation for 10 minutes at 3000 rpm;
- reading of the optical density at 540 nm on 150 μl of supernatant.

A subject of the invention is also a purified or isolated nucleic acid encoding at least one polypeptide as described above. Table 1 below comprises the identifications of the nucleic and peptide sequences for the EG2 genes, and the genes of the putative endoglucanase 2 of *Botryotinia fuckeliana* (BF gene) and of the putative endoglucanase 2 of *Sclerotinia sclerotiorum* (SS gene), and also for the nucleic and polypeptide sequences of the invention.

Preferably, said purified or isolated nucleic acid can be chosen from the following sequences: SEQ ID NO: 3, SEQ ID NO: 5, SEQ ID NO: 7, SEQ ID NO: 9, SEQ ID NO: 11;

SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33.

TABLE 1

| Clones | Nucleic acid | Polypeptide |
|---|---|---|
| EG2 (wild-type) | SEQ ID NO: 1 | SEQ ID NO: 2 |
| 37D12 | SEQ ID NO: 3 | SEQ ID NO: 4 |
| 45A7 | SEQ ID NO: 5 | SEQ ID NO: 6 |
| 46H1 | SEQ ID NO: 7 | SEQ ID NO: 8 |
| 50F10 | SEQ ID NO: 9 | SEQ ID NO: 10 |
| 108G5 | SEQ ID NO: 11 | SEQ ID NO: 12 |
| 140F7 | SEQ ID NO: 13 | SEQ ID NO: 14 |
| 146C4 | SEQ ID NO: 15 | SEQ ID NO: 16 |
| 149E4 | SEQ ID NO: 17 | SEQ ID NO: 18 |
| 173C6 | SEQ ID NO: 19 | SEQ ID NO: 20 |
| 191H11 | SEQ ID NO: 21 | SEQ ID NO: 22 |
| 222E1 | SEQ ID NO: 23 | SEQ ID NO: 24 |
| 225C7 | SEQ ID NO: 25 | SEQ ID NO: 26 |
| 227C4 | SEQ ID NO: 27 | SEQ ID NO: 28 |
| 229D1 | SEQ ID NO: 29 | SEQ ID NO: 30 |
| 231C9 | SEQ ID NO: 31 | SEQ ID NO: 32 |
| 330F9 | SEQ ID NO: 33 | SEQ ID NO: 34 |
| BF Gene | SEQ ID NO: 35 | SEQ ID NO: 36 |
| SS Gene | SEQ ID NO: 37 | SEQ ID NO: 38 |

The invention also relates to a vector comprising a nucleic acid as described above.

According to the invention, the term "vector" is intended to mean any DNA sequence into which it is possible to insert fragments of foreign nucleic acid, the vectors making it possible to introduce foreign DNA into a host cell. As vectors, mention may be made, nonexhaustively, of: plasmids, cosmids, yeast artificial chromosomes (YACs), bacterial artificial chromosomes (BACs), P1 bacteriophage-derived artificial chromosomes (PACs) or virus-derived vectors.

According to the invention, the nucleic acid as described above may be functionally linked to a promoter, a terminator or any other sequence required for its expression in the host cell.

The vector according to the invention may also carry a selectable marker. The term "selectable marker" is intended to mean a gene of which the expression confers on the cells that contain it a characteristic which makes it possible to select them. It is, for example, a gene for resistance to antibiotics.

A subject of the invention is also an isolated host cell comprising either at least one of the polypeptides as described above, or at least one of the nucleic acids as described above or at least one of the vectors as described above.

Those skilled in the art will be able to introduce one of the polypeptides, one of the nucleic acids or one of the vectors as described above into the host cell by means of well-known conventional methods. For example, mention may be made of treatment with calcium chloride, electroporation, or the use of a particle gun.

According to one embodiment, those skilled in the art will be able to introduce into the host cell, and by means of conventional methods, several copies of a nucleic acid encoding a polypeptide having an improved endoglucanase activity according to the invention.

According to one embodiment, the isolated host cell as described above is chosen from *Trichoderma, Aspergillus, Neurospora, Humicola, Myceliophthora, Chrysosporium, Penicillium, Fusarium, Thermomonospora, Bacillus, Pseudomonas, Escherichia, Clostridium, Cellulomonas, Streptomyces, Yarrowia, Pichia* and *Saccharomyces.*

According to one preferred embodiment, the isolated host cell as described above is chosen from *Trichoderma reesei, Trichoderma viridae, Trichoderma koningii, Aspergillus niger, Aspergillus nidulans, Aspergillus wentii, Aspergillus oryzae, Aspergillus phoenicis, Myceliophthora thermopila, Chrysosporium lucknowense, Neurospora crassa, Humicola grisae, Penicillium pinophilum, Penicillium oxalicum, Escherichia coli, Clostridium acetobutylicum, Clostridium saccharolyticum, Clostridium benjerinckii, Clostridium butylicum, Pichia pastoris, Yarrowia lipolityca* and *Saccharomyces cerevisiae.*

According to one preferred embodiment, the isolated host cell as described above is chosen from *Trichoderma reesei* and *Saccharomyces cerevisiae.*

A subject of the invention is also the use of any one of the polypeptides described above, for the hydrolysis of cellulose.

A subject of the invention is also the use of any one of the polypeptides described above, for the production of biofuel.

According to the invention, the term "biofuel" can be defined as any product resulting from the conversion of biomass and which can be used for energy purposes. Furthermore and without wishing to be limited, mention may be made, by way of example, of biogases, products which can be incorporated (optionally after subsequent conversion) into a fuel or may be a fuel in its own right, such as alcohols (ethanol, butanol and/or isopropanol depending on the type of fermentative organism used), solvents (acetone), acids (butyric acid), lipids and derivatives thereof (short-chain or long-chain fatty acids, fatty acid esters), and also hydrogen.

Preferably, the biofuel according to the invention is an alcohol, for example ethanol, butanol and/or isopropanol. More preferentially, the biofuel according to the invention is ethanol.

In another embodiment, the biofuel is biogas.

In another embodiment, the product is a molecule of interest to the chemical industry, for instance another alcohol such as 1,2-propanediol, 1,3-propanediol, 1,4-butanediol, 2,3-butanediol, organic acids such as acetic acid, propionic acid, acrylic acid, butyric acid, succinic acid, malic acid, fumaric acid, citric acid or itaconic acid, or hydroxy acids such as glycolic acid, hydroxypropionic acid or lactic acid.

Described below is an embodiment of production of an enzymatic cocktail that is useful for the hydrolysis of lignocellulose. The strains of filamentous fungi, preferably *Trichoderma*, more preferentially *T. reesei*, capable of expressing at least one polypeptide according to the invention are cultured in fermentors, in the presence of a carbon-based substrate, such as lactose or glucose, chosen for growth of the microorganism. In one embodiment, this carbon-based substrate, depending on its nature, is introduced into the fermentor before sterilization or is sterilized separately and introduced into the fermentor after sterilization of the latter so as to obtain an initial concentration of 20 to 35 g/l.

An aqueous solution containing the substrate chosen for the production of the enzymes is then added. An enzymatic composition which acts on the lignocellulosic biomass produced by the fungi is finally recovered by filtration of the culture medium. In this composition are, in particular, the β-glucosidase, the exoglucanase and the endoglucanase according to the invention. In one embodiment, the aqueous solution containing the substrate chosen for the production of the enzymes is prepared at the concentration of 200-250 g/l and also contains an inducer substrate such as lactose.

This aqueous solution is injected after the exhaustion of the initial carbon-based substrate so as to provide an optimized amount of between 35 and 45 mg/g of cells ("fed batch"). During this "fed batch" phase, the residual concentration of sugar in the culture medium is less than 1 g/l and the enzymes which act on the lignocellulosic biomass are secreted by the fungus. The latter can be recovered by filtration of the culture medium.

A subject of the invention is an enzymatic composition capable of acting on lignocellulosic biomass, said enzymatic composition preferably being produced by filamentous fungi and comprising at least one polypeptide having improved endoglucanase activity relative to the endoglucanase activity of the wild-type EG2 protein. The term "filamentous fungi" is intended to mean in particular *Trichoderma*, more preferentially *T. reesei*.

Finally, a subject of the invention is a process for producing biofuel from biomass, comprising the following successive steps:

- suspension, in an aqueous phase, of the biomass to be hydrolyzed;
- hydrolysis, in the presence of an enzymatic composition, of the lignocellulosic biomass as described above so as to produce a hydrolysate containing glucose;
- fermentation of the glucose of the hydrolysate so as to produce a fermentation must;
- separation of the biofuel from the fermentation must.

In one embodiment, the biomass to be hydrolyzed is suspended in an aqueous phase in a proportion of from 6% to 40% of solids, preferably 20% to 30%. The pH is adjusted to between 4 and 5.5; preferably, between 4.8 and 5.2, and the temperature is adjusted to between 40 and 60° C., preferably between 45 and 50° C. The hydrolysis reaction is initiated by adding the enzymatic composition which acts on lignocellulosic biomass; the amount normally used is from 10 to 30 mg of excreted proteins per gram of pretreated substrate or less. The reaction generally lasts from 15 to 48 hours. The reaction is monitored by assaying the sugars released, in particular glucose. The solution of sugars is separated from the nonhydrolyzed solid fraction, essentially consisting of lignin, by filtration or centrifugation and is subsequently treated in a fermentation unit.

In one embodiment, it will be possible to separate the biofuel from the fermentation must for example by distillation.

Another subject of the invention is a process for producing biofuel from biomass, characterized in that it comprises the following successive steps:

- suspension, in an aqueous phase, of the biomass to be hydrolyzed;
- simultaneous addition of an enzymatic composition as defined above and of a fermentative organism, preferably at a temperature of between 30° C. and 35° C., so as to produce a fermentation must;
- separation of the biofuel from the fermentation must.

Preferably, the enzymatic composition and the fermentative organism are added simultaneously and then incubated in a temperature of between 30° C. and 35° C. so as to produce a fermentation must.

According to this embodiment, the cellulose present in the biomass is converted to glucose, and at the same time, in the same reactor, the fermentative organism (for example a yeast) converts the glucose to final product according to an SSF (Simultaneous Saccharification and Fermentation) process known to those skilled in the art. Depending on the metabolic and hydrolytic capacities of the fermentative organism, a more or less large amount of exogenous cellulolytic mixture may need to be added in order for the operation to proceed correctly.

In another embodiment, the fermentative organism also produces the polypeptide which is the subject of the invention by secretion or at the surface of its cell, optionally together with other enzymes which act on lignocellulosic biomass, thus limiting or eliminating the need for enzymes produced by the filamentous fungus.

Preferably, the fermentative organism is a host cell as described above.

Thus, preferably, a subject of the invention is a process for producing biofuel from biomass, comprising the following successive steps:

- suspension, in an aqueous phase, of the biomass to be hydrolyzed;
- addition of one or more host cells as described above, with a fermentative organism and/or an enzymatic composition as described above, so as to produce a fermentation must;
- separation of the biofuel from the fermentation must.

Preferably, the host cells with the enzymatic composition and/or the fermentative organism are added and then incubated at a temperature of between 30° C. and 35° C. so as to produce a fermentation must.

The use of the polypeptide having an improved endoglucanase activity according to the present invention thus has the advantage of obtaining a better glucose production yield. Thus, the present invention makes it possible to use less enzyme than previously, which provides an advantage from an economic point of view.

Other aspects, subjects, advantages and characteristics of the invention will be presented on reading the nonrestrictive description which follows and which describes preferred embodiments of the invention, given by means of examples and of the figures.

Figure 4:
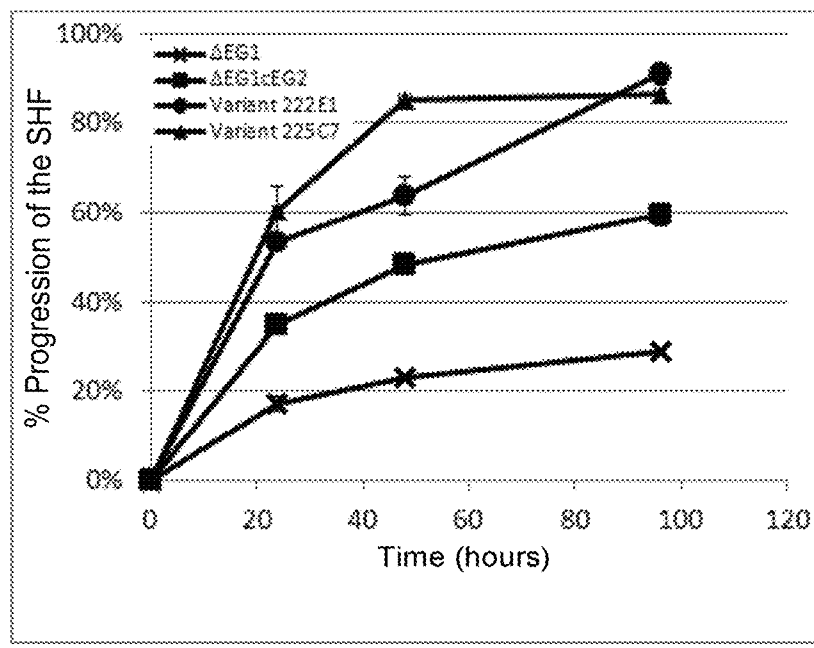

FIG. 4 is a graph presenting the results of SHF for the cocktail derived from the strain 222E1 (SEQ ID NO: 24) and the cocktail derived from the strain 225C7/7 (SEQ ID NO: 26), a reference cocktail produced by the strain CL847 ΔEG1 (ΔEG1) supplemented with β-glucosidase and another reference cocktail produced by the strain CL847 ΔEG1 retransformed with the EG2 reference gene (ΔEG1cEG2) supplemented with β-glucosidase.

Figure 5:
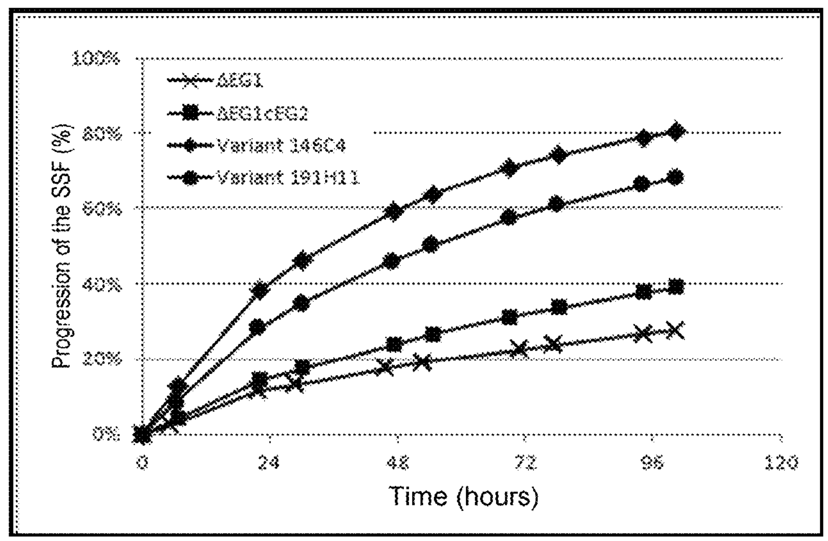

FIG. 5 is a graph presenting the results of SSF for the cocktail derived from the strain 146C4/7 (SEQ ID NO: 16) and for the cocktail derived from the strain 191H11/9 (SEQ ID NO:22), a reference cocktail produced by the strain CL847 ΔEG1 (ΔEG1) supplemented with β-glucosidase and another reference cocktail produced by the strain CL847

ΔEG1 retransformed with the EG2 reference gene (ΔEG1cEG2) supplemented with β-glucosidase.

Figure 6:
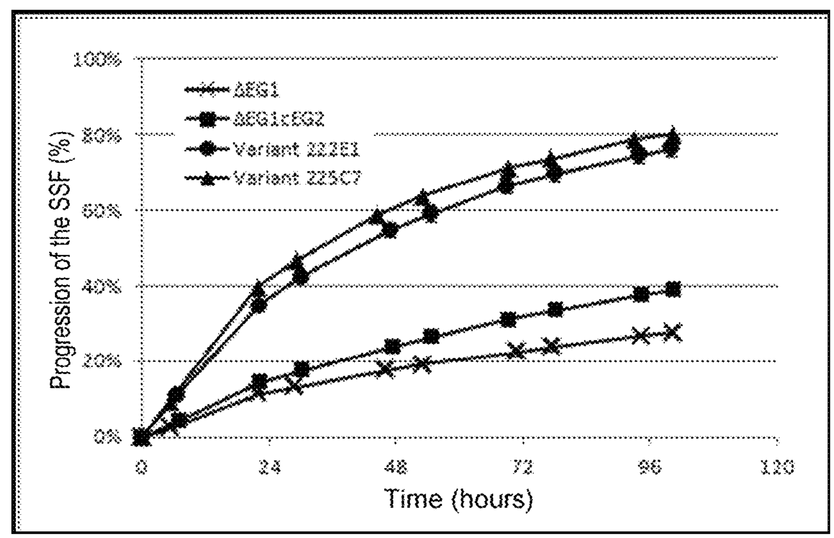

FIG. 6 is a graph presenting the average of the results of SSF for the 3 cocktails derived from the strains 222E1/1, 222E1/2 and 222E1/7 (SEQ ID NO: 24) and the results for the cocktail derived from the strain 225C7/7 (SEQ ID NO: 26), a reference cocktail produced by the strain CL847 ΔEG1 (ΔEG1) supplemented with β-glucosidase and another reference cocktail produced by the strain CL847 ΔEG1 retransformed with the EG2 reference gene (ΔEG1cEG2) supplemented with β-glucosidase.

EXAMPLES

Example 1: Evolution by L-Shuffling

The sequence of the *Trichoderma reesei* endoglucanase 2 (EG2) gene was subjected to a round of L-shuffling according to the patented process described in EP1104457B1 with the genes of the putative endoglucanase 2 of *Botryotinia fuckeliana* (BF gene) and of the putative endoglucanase 2 of *Sclerotinia sclerotiorum* (SS gene) each having 64% identity with the EG2 reference gene (SEQ ID NO: 1).

1—High-Throughput Screening

A high-throughput screening test was developed in order to select the best clones resulting from the L-shuffling, i.e. those exhibiting at least 20% improvement in the endoglucanase activity relative to the *T. reesei* enzyme.

The high-throughput screening test was carried out according to the following steps:

- isolation on agar of the *E. coli* clones expressing the variants of the recombinant enzyme according to the invention and preculturing of said colonies in LB medium overnight at 37° C.;
- inoculation of an LB medium at 6% with the preculture, then incubation for 5 h at 37° C., then 17 h at 20° C.;
- centrifugation for 10 minutes at 3000 rpm;
- lysis of the cells by addition of 80 μl of a solution of lysozyme at 1 mg/ml in a 0.1 M citrate phosphate buffer at pH 5;
- incubation for 4 h at ambient temperature;
- addition of 80 μl of 0.1 M citrate phosphate buffer, pH 5, containing 1% of carboxymethylcellulose;
- incubation for 3 h at 35° C.;
- centrifugation for 10 minutes at 3000 rpm;
- removal of 100 μl of supernatant;
- addition of 100 μl of DNS reagent;
- incubation for 10 minutes at 100° C. and then 5 minutes on ice;
- reading of the OD at 540 nm on 120 μl.

Under these screening conditions, an improvement in the endoglucanase activity (increase in the OD at 540 nm) relative to the EG2 reference enzyme (SEQ ID NO: 2) was found in the clones 37D12, 45A7, 46H1, 50F10, 108G5, 140F7, 146C4, 149E4, 173C6, 191H11, 222E1, 225C7, 227C4, 229D1, 231C9 and 330F9.

2—Determination of the Improvement in the Endoglucanase Activity 2-1/on the Carboxymethylcellulose (CMC) Substrate In order to estimate the kcat of the clones 37D12, 45A7, 46H1, 50F10, 108G5, 140F7, 146C4, 149E4, 173C6, 191H11, 222E1, 225C7, 227C4, 229D1, 231C9 and 330F9 compared with the reference enzymes, the following procedure is carried out:

- preparation of a stock culture of *E. coli* expressing a recombinant enzyme according to the invention overnight at 37° C.;
- inoculation of an LB culture medium with 1% of stock culture at 37° C. until an optical density at 600 nm of 0.4 is obtained;
- culture of said cells at 20° C. for 18 h;
- centrifugation for 5 minutes at 7900 rpm;
- resuspension of the cell pellets with 0.1 M citrate phosphate buffer at pH 5 containing 1 mg/ml of lysozyme (final $OD_{600}$ 100);
- incubation of the resuspended cells for 30 minutes on ice;
- lysis of the cells by means of three cycles of freezing/thawing;
- fractionation of the DNA by sonication for 3 seconds at power 5;
- centrifugation for 30 minutes at 13000 rpm;
- incubation of 100 μl of breaking supernatant with 100 μl of 0.1 M citrate phosphate buffer at pH 5 containing 1% of CMC for 1 h at 35 and 50° C.;
- removal of 100 μl of reaction;
- addition of 100 μl of DNS reagent;
- incubation for 5 minutes at 100° C.;
- incubation for 3 minutes on ice;
- centrifugation for 10 minutes at 3000 rpm;
- reading of the optical density at 540 nm on 150 μl.

According to the invention, the kcat values are calculated in the following way:

- expressing the ODs at 540 nm as a function of the amount of protein of interest (in nM);
- subtracting the value of the negative control;
- dividing by the coefficient of the glucose standard range (various amounts of glucose are revealed with DNS)
- dividing by the reaction time.

Table 2 presents the kcat values and also the improvement factor relative to the EG2 reference protein (SEQ ID NO: 2) obtained for the clones 37D12, 45A7, 46H1, 50F10, 108G5, 140F7, 146C4, 149E4, 173C6, 191H11, 222E1, 225C7, 227C4, 229D1, 231C9 and 330F9 under the experimental conditions of the activity test on CMC.

TABLE 2

| Endoglucanase activity on CMC | | | | | |
|---|---|---|---|---|---|
| | | 35° C. | | 50° C. | |
| | Clone | Kcat ($min^{-1}$) | Improvement factor | Kcat ($min^{-1}$) | Improvement factor |
| L-shuffling clones | 37D12 | 2717.1 | 2.27 | 5574.1 | 2.73 |
| | 45A7 | 3183.8 | 2.66 | 6500 | 3.18 |
| | 46H1 | 1933.1 | 1.61 | 3124.6 | 1.53 |
| | 50F10 | 2864.8 | 2.39 | 5284.6 | 2.59 |
| | 108G5 | 2062.2 | 1.72 | 4235.5 | 2.07 |
| | 140F7 | 2024 | 1.69 | 4079.6 | 2.00 |
| | 146C4 | 1692.3 | 1.41 | 3221.5 | 1.58 |
| | 149E4 | 3132.9 | 2.61 | 5316.8 | 2.60 |
| | 173C6 | 2472.9 | 2.06 | 6596.2 | 3.23 |
| | 191H11 | 3247.8 | 2.71 | 5275.3 | 2.58 |
| | 222E1 | 4484.5 | 3.74 | 9036.8 | 4.43 |
| | 225C7 | 2778.2 | 2.32 | 4026 | 1.97 |
| | 227C4 | 2340.3 | 1.95 | 3671.6 | 1.80 |
| | 229D1 | 2737.3 | 2.28 | 6597 | 3.23 |
| | 231C9 | 2344 | 1.95 | 3441.2 | 1.69 |
| | 330F9 | 2172.8 | 1.81 | 4222.8 | 2.07 |
| Reference protein | EG2 | 1199.05 | 1 | 2041.7 | 1 |

The results show significant improvements in enzymatic activity relative to the EG2 reference enzyme (SEQ ID NO: 2) for these clones.

2-2/on the Phosphoric Acid Swollen Cellulose (PASC) Substrate

The improvement in activity of the clones 37D12, 45A7, 46H1, 50F10, 108G5, 140F7, 146C4, 149E4, 173C6, 191H11, 222E1, 225C7, 227C4, 229D1, 231C9 and 330F9 was then confirmed on a second substrate: phosphoric acid swollen cellulose (PASC).

Table 3 presents the kcat values and also the improvement factors obtained for the clones 37D12, 45A7, 46H1, 50F10, 108G5, 140F7, 146C4, 149E4, 173C6, 191H11, 222E1, 225C7, 227C4, 229D1, 231C9 and 330F9 at 50° C. relative to the EG2 reference protein (SEQ ID NO: 2) under the experimental conditions of the activity test on PASC.

TABLE 3

Endoglucanase activity on PASC

| | | 50° C. | |
|---|---|---|---|
| | Clone | Kcat ($min^{-1}$) | Improvement factor |
| L-shuffling clones | 37D12 | 4.51 | 1.12 |
| | 45A7 | 5.86 | 1.45 |
| | 46H1 | 6.56 | 1.62 |
| | 50F10 | 5.04 | 1.25 |
| | 108G5 | 8.49 | 2.10 |
| | 140F7 | 7.82 | 1.94 |
| | 146C4 | 8.12 | 2.01 |
| | 149E4 | 5.96 | 1.48 |
| | 173C6 | 5.87 | 1.45 |
| | 191H11 | 8.38 | 2.07 |
| | 222E1 | 5.14 | 1.27 |
| | 225C7 | 5.44 | 1.35 |
| | 227C4 | 4.76 | 1.18 |
| | 229D1 | 3.91 | 0.97 |
| | 231C9 | 4.62 | 1.14 |
| | 330F9 | 4.3 | 1.06 |
| Reference protein | EG2 | 4.04 | 1 |

The results show significant improvements in enzymatic activity relative to the EG2 reference enzyme (SEQ ID NO: 2) for these clones.

2-3/on the Sigmacell Substrate

The improvement in the clones 37D12, 45A7, 46H1, 50F10, 108G5, 140F7, 146C4, 149E4, 173C6, 191H11, 222E1, 225C7, 227C4, 229D1, 231C9 and 330F9 was also evaluated on a third substrate: Sigmacell. The test protocol is the same as that described previously with the CMC substrate. The incubation with the substrate takes place for 24 h at 50° C.

Table 4 presents the kcat value and also the improvement factors obtained for the clones 37D12, 45A7, 46H1, 50F10, 108G5, 140F7, 146C4, 149E4, 173C6, 191H11, 222E1, 225C7, 227C4, 229D1, 231C9 and 330F9 at 50° C. relative to the EG2 reference protein (SEQ ID NO: 2) under the experimental conditions of the activity test on Sigmacell.

TABLE 4

Endoglucanase activity on Sigmacell

| | | 50° C. | |
|---|---|---|---|
| | Clone | Kcat ($min^{-1}$) | Improvement factor |
| L-shuffling clones | 37D12 | 6.84 | 1.20 |
| | 45A7 | 6.54 | 1.15 |
| | 46H1 | 6.04 | 1.06 |
| | 50F10 | 7.12 | 1.25 |
| | 108G5 | 5.95 | 1.05 |
| | 140F7 | 6.9 | 1.21 |
| | 146C4 | 9.3 | 1.63 |
| | 149E4 | 5.71 | 1.00 |
| | 173C6 | 5.85 | 1.03 |
| | 191H11 | 5.99 | 1.05 |
| | 222E1 | 9.16 | 1.61 |
| | 225C7 | 7.16 | 1.26 |
| | 227C4 | 7.22 | 1.27 |
| | 229D1 | 6.25 | 1.10 |
| | 231C9 | 6.46 | 1.14 |
| | 330F9 | 5.99 | 1.05 |
| Reference protein | EG2 | 5.69 | 1 |

The results show that the improvement in activity for the clones 37D12, 45A7, 46H1, 50F10, 108G5, 140F7, 146C4, 149E4, 173C6, 191H11, 222E1, 225C7, 227C4, 229D1, 231C9 and 330F9 can be seen relative to the EG2 reference enzyme (SEQ ID NO: 2) with the Sigmacell substrate.

Example 2

The variants 146C4, 191H11, 222E1 and 225C7, and also the EG2 reference gene of *T. reesei* (SEQ ID NO: 2) were cloned between the cbh1 promoter and terminator in the pUT1040 plasmid containing a phleomycin resistance gene as marker, by means of a BamHI/XhoI double digestion. 5 µg of each vector were used for the transformation of the *T. reesei* strain CL847ΔEG1. Protoplasts were transformed according to a conventional method known to those skilled in the art, by calcium and PEG shock, with 5 µg of each construct. The transformants were selected on PDA/sucrose selective medium containing 30 µg/l of phleomycin. After three successive subculturings making it possible to obtain pure clones, between eleven and fifteen clones were obtained for each of the variants. All of the clones were cultured in F45 medium (800 µl 85% $H_3PO_4$, 4.2 g $(NH_4)_2SO_4$, 0.3 g $MgSO_4.7H_2O$, 0.75 g CornSteep, 1 ml Oligo Ferment, 6 g potassium phthalate, pH 5.8-6) with 5 g/l glucose and 10 g/l sorbose as carbon substrate and inducer. After 7 days of culture at 30° C., the supernatant is removed and the equivalent of 10 mg/l of proteins, measured by the Lowry method, is used for an activity test on carboxymethylcellulose.

For the activity measurements, 150 µl of a 2% CMC solution in 50 mM citrate buffer, pH 4.8, are mixed with 150 µl of citrate buffer containing 10 mg/l of proteins. The reaction is incubated at 50° C. and 35° C. for 10 min and then inactivated in a boiling water bath. After centrifugation for 5 minutes, 20 µl are removed in order to assay reducing sugars using 3,5-dinitrosalicylic acid (DNS). The reduction of the DNS and the formation of 3-amino-5-nitrosalicylic acid are monitored by reading the absorption at 540 nm and the reducing sugars are quantified using a glucose range.

Table 5 summarizes the activities (expressed in µmol glucose equivalent/mg of protein/min) obtained for the best clones for each variant. The value for the strain ΔEG1 transformed with the native EG2 gene (ΔEG1cEG2) is an average of the best four clones.

TABLE 5

| Endoglucanase activity on CMC | | | | |
|---|---|---|---|---|
| Clone | Specific activity 50° C. (μmol/mg/min) | Variant/ΔEG2cEG2 ratio 50° C. | Specific activity 35° C. (μmol/mg/min) | Variant/ΔEG2cEG2 ratio 35° C. |
| ΔEG2cEG2 | 10.8 ± 1.8 | | 8.6 ± 2.2 | |
| 191H11/2 | 23.1 ± 1.8 | 2.1 | 9.9 ± 2.8 | 1.2 |
| 191H11/9 | 21.9 ± 4.0 | 2.0 | 10.8 ± 1.6 | 1.3 |
| 191H11/12 | 17.4 ± 0.4 | 1.6 | 9.7 ± 2.0 | 1.1 |
| 146C4/1 | 12.0 ± 1.1 | 1.1 | 8.5 ± 0.7 | 1.0 |
| 146C4/6 | 11.7 ± 0.4 | 1.1 | 8.6 ± 1.2 | 1.0 |
| 146C4/7 | 16.1 ± 1.1 | 1.5 | 11.9 ± 3.2 | 1.4 |
| 222E1/1 | 21.4 ± 0.8 | 2.0 | 13.9 ± 3.3 | 1.6 |
| 222E1/2 | 18.3 ± 1.3 | 1.7 | 13.7 ± 1.4 | 1.6 |
| 222E1/4 | 13.5 ± 0.6 | 1.3 | 10.4 ± 0.8 | 1.2 |
| 222E1/7 | 16.2 ± 1.3 | 1.5 | 11.4 ± 0.3 | 1.3 |
| 225C7/7 | 11.4 ± 0.1 | 1.1 | 10.3 ± 3.3 | 1.2 |
| 225C7/9 | 14.7 ± 0.4 | 1.4 | 8.1 ± 1.4 | 0.9 |

For each variant, at least one clone has a CMCase activity greater than the strain ΔEG1cEG2 at 35° C. or at 50° C., the best clones showing twice as much activity as the strain ΔEG1cEG2.

Example 3: Recombinant Expression of the EG2 Reference Endoglucanase and of the 222E1 and 225C7 Variants in *Saccharomyces cerevisiae*

1—Production of the EG2 Reference Endoglucanase Reference Protein and the 222E1 Variant Thereof in the Extracellular Medium The EG2 reference endoglucanase gene of *Trichoderma reesei* (SEQ ID NO: 1) and the genes of the 222E1 and 225C7 (SEQ ID NO: 23 and 25 respectively) variants were cloned, without their signal peptide, into the pESC-LeuαΔmyc vector (CNRS-CERMAV). This construct allows the expression of the proteins in the culture medium of the *Saccharomyces cerevisiae* strain EBY100, which is auxotrophic for leucine and tryptophan (Boder E T and Wittrup K D, Biotechnol Prog, 1998, 14:55-62). This plasmid makes it possible to place the expression of the genes under the control of the galactose-inducible GAL1 promoter and possesses the auxotrophy selectable marker gene (Leu2) which allows the selection of the transformants.

The transformation of *Saccharomyces cerevisiae* EBY100 was carried out according to the conventional methods known to those skilled in the art (transformation of yeasts by heat shock and lithium acetate). The transformants were selected on 0.67% YNB-2% Glc-0.01% Trp medium.

One transformant for each gene (Scα-EG2, Scα-222E1 and Scα-225C7) was used to inoculate 15 ml of a 0.67% YNB-2% Glc-SD-0.01% Trp minimum medium. SD is a mixture of amino acids (40 mg/l of adenine sulfate; 20 mg/l of L-arginine; 100 mg/l of aspartic acid; 100 mg/l of L-glutamic acid; 20 mg/l of L-histidine; 30 mg/l of L-lysine; 20 mg/l of L-methionine; 50 mg/l of L-phenylalanine; 375 mg/l of L-serine; 200 mg/l of L-threonine; 30 mg/l of L-tyrosine; 150 mg/l of L-valine and 20 mg/l of uracil). After 24 h of preculture at 30° C. with shaking at 220 rpm, the three strains of Scα-EG2, Scα-222E1 and Scα-225C7 were used to inoculate ($OD_{600}$ of 0.5) 150 ml of 0.67% YNB-2% Gal-SD-0.01% Trp medium. The cultures were incubated at 25° C. with shaking at 220 rpm. After 8 h of incubation, 6 ml of sodium citrate at pH 5.6 were added to each culture in order to stabilize the pH at 5.

After 4 days of incubation, 20 ml of culture were removed. The culture supernatant was obtained after centrifugation at 3000 g, at 4° C., for 5 min.

2-Determination of the Endoglucanase Activity on β-Nitrophenyl-β-Cellotrioside

The endoglucanase activity of the culture supernatants was measured by hydrolysis of the pNPC3 substrate in a volume of 450 μl under the following conditions:

50 mM of citrate buffer at pH 5

2 mM of pNPC3

56.3 μl of culture supernatant from the Scα-EG2, Scα-221E1 and Scα-225C7 strains;

incubation at 35° C. for 6 h.

The reaction was stopped by adding 100 μl of 1 M of sodium carbonate to 100 μl of hydrolysis reaction. The concentration of para-nitrophenol (pNP) released by hydrolysis of pNPC3 was determined by measuring the absorbance at 415 nm by comparison with a para-nitrophenol standard range (linear from 0.36 μM to 360 μM).

Figure 1:
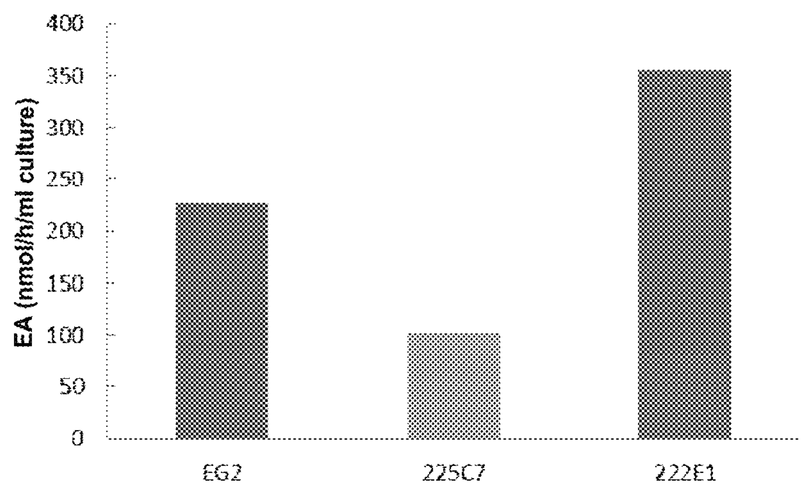
FIG. 1 is a graph representing the hydrolysis of p-nitrophenyl-β-cellotrioside (pNPC3) by the EG2 reference endoglucanase (SEQ ID NO: 2) and mutants 222E1 and 225C7 (SEQ ID NO: 24 and 26, respectively) secreted into the culture medium by the strains Scα-EG2 and Scα-222E1 and Scα-225C7, respectively.

The results of FIG. 1 show that the Scα-222E1 strain has an endoglucanase activity improved by a factor of 1.6 relative to the Scα-EG2 strain which expresses the EG2 reference enzyme (SEQ ID NO: 2). The strain Scα-225C7 was found, for its part, to be less effective for the hydrolysis of this substrate.

3—Determination of the Endoglucanase Activity on Carboxymethylcellulose

The endoglucanase activity of the culture supernatants was measured by hydrolysis of carboxymethylcellulose (CMC) in a volume of 700 μl under the following conditions:

50 mM of citrate buffer at pH 5

1% of CMC

210 μl of culture supernatant of the Scα-EG2, Scα-222E1 and Scα-225C7 strains dialyzed against 50 mM citrate buffer, pH 5, on a 10 kDa membrane, and concentrated two-fold incubation at 35° C. for 24 h.

The reaction was stopped by adding 150 μl of DNS reagent to 100 μl of hydrolysis reaction. After heating for 5 minutes at 100° C. and cooling in ice, the amount of reducing sugars released was determined by measuring the absorbance at 550 nm by comparison with a standard range produced with glucose.

Figure 2:
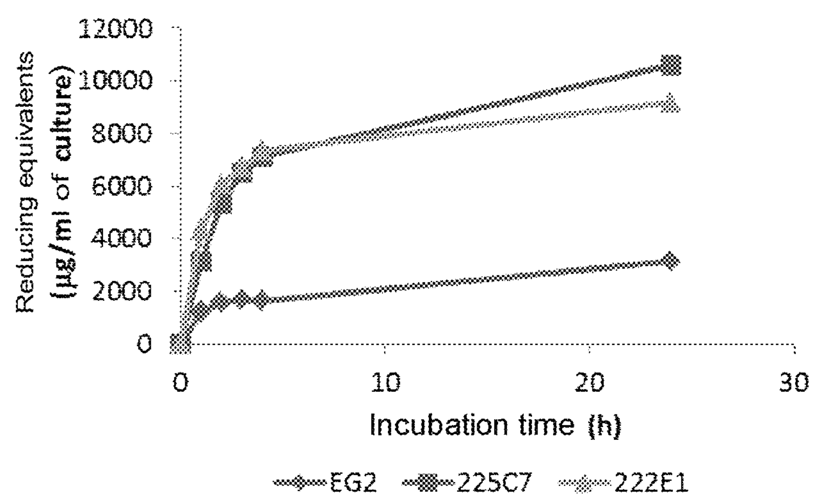
FIG. 2 is a graph representing the hydrolysis of 1% CMC by the EG2 reference endoglucanase (SEQ ID NO: 2) and mutants 222E1 and 225C7 (SEQ ID NO: 24 and 26 respectively) secreted into the culture medium by the strains Scα-EG2 and Scα-222E1 and Scα-225C7, respectively.

The results of FIG. 2 indicate that the amount of reducing sugars released by the action of the variants of the strains Scα-222E1 and Scα-225C7 is greater than with the strain Scα-EG2. Thus, after 1 h of hydrolysis of the CMC, the improvement factor at 35° C. on this substrate is 3.5 for Scα-222E1 and 2.6 for Scα-225C7 relative to Scα-EG2. Beyond this incubation time, the CMC continues to be hydrolyzed by the two variants, whereas the reaction rate becomes virtually zero in the presence of the EG2 reference protein (SEQ ID NO: 2).

Example 4: Production of Enzymes by *T. reesei* in Fed Flasks

The reference strains and those having the best activity on CMC (CL847, ΔEG1, ΔEG1cEG2, 146C4/7, 191H11/9, 222E1/1, 222E1/2, 222E1/7, 225C7/7) were cultured in 250 ml Erlenmeyer flasks. 55 ml of F45 medium (10 g/l of dipotassiumphthalate buffer, pH 6, 4.2 g/l $(NH_4)_2SO_4$, 300 mg/l $MgSO_4.7H_2O$, 150 mg/l $CaCl_2.2H_2O$, 1.5 g/l cornsteep, 0.07% orthophosphoric acid, 5 mg/l $FeSO_4$, 1.4 mg/l $MnSO_4$, 1.4 mg/l $ZnSO_4$, 3.7 mg/l $CoCl_2$ and 12.5 g/l glucose) are inoculated and shaken at 150 rpm and 30° C.

The production is carried out in two phases: a batch phase on glucose and a fed-batch phase on lactose. Regular samples make it possible to determine the moment in which the glucose concentration goes below 3 g/l. At this stage, fed-batch feeding using a syringe driver (6-way) is initiated. The cultures are fed with a solution of 50 g/l lactose and 0.3% $NH_3$ at a flow rate of 40 mg of sugar/g of biomass per hour. Daily samples are taken in order to determine the pH, the dry weight and the concentration of proteins in the supernatant. After 5 days of fed-batch culture, the culture is filtered through a 0.45 μm filter and the supernatant is frozen.

The final concentration of proteins was about 3 to 4 g/l. If the concentration was below 3 g/l, the supernatants were concentrated on a column (Vivaspin MWCO5, Sartorius).

Example 5: Effectiveness of the Enzymes Resulting from the L-Shuffling in Hydrolysis of Lignocellulosic Biomass According to an SHF Process The reference substrate used is a wheat straw which has undergone a vapor-explosion pretreatment (19 bar—3 minutes) after acid impregnation with 0.01% $H_2SO_4$ for 10 hours, and being washed, neutralized at pH 5, pressed and dried. The characteristics thereof are presented in Table 9.

TABLE 6

Composition of the straw used for the hydrolysis tests

| Composition | % w/w |
|---|---|
| WIS | 97.52 |
| Ash content | 5 |
| Cellulose | 51.7 |
| Corrected xylans | 3.57 |
| Hemicellulose | 4.14 |
| Klason lignin (overestimated) | 36.49 |
| Acetyl | 0.6 |

The hydrolyses were carried out at 10% of solids w/w, i.e. an equivalent of 5.4% cellulose w/w.

The protein content is fixed at 10 mg/g of solids, i.e. approximately 19 mg/g of cellulose. The concentration of the enzymatic cocktails was measured by the Lowry method using BSA as reference. Each cocktail was supplemented with β-glucosidase activity in an amount of 120±2 IU/g of cellulose, by adding SP188 β-glucosidase (Novozymes).

The tests are carried out in Eppendorf tubes having a 2 ml working capacity (1 g reaction capacity) containing:

- 0.11±0.001 g of washed straw substrate,
- 0.9±0.02 ml of hydrolysis reaction medium composed of 50 mM acetate buffer, pH 4.8, and chloramphenicol (0.05 g/l),
- between 0.1 and 0.2±0.02 g of enzymatic cocktail depending on their protein content.

The enzymatic hydrolyses are carried out at 45±2° C. with vortex stirring at 900 revolutions per minute in an Eppendorf Thermomixer Comfort.

All the tests are carried out in duplicate with sampling times fixed at t 24, 48 and 96 hours with, for some, samples taken at t 72 hours.

At each sampling time, the hydrolysates are boiled for 5 minutes in the sacrificed Eppendorf tubes. These tubes are then cooled and centrifuged. The glucose assay is performed by HPLC. In parallel, the solid residues of each Eppendorf tube are washed and centrifuged 3 times before being dried at 105° C. for 24 hours so as to evaluate the WIS (Water Insoluble Solids). The hydrolysis yield is calculated taking into account the WIS.

The cocktails resulting from example 4 were evaluated. Two control tests are carried out with the reference cocktails also supplemented with β-glucosidase for comparison: a cocktail produced by the strain CL847 ΔEG1 (ΔEG1) and a cocktail produced by the strain CL847 ΔEG1 retransformed with the EG2 reference gene (ΔEG1cEG2).

Figure 3:
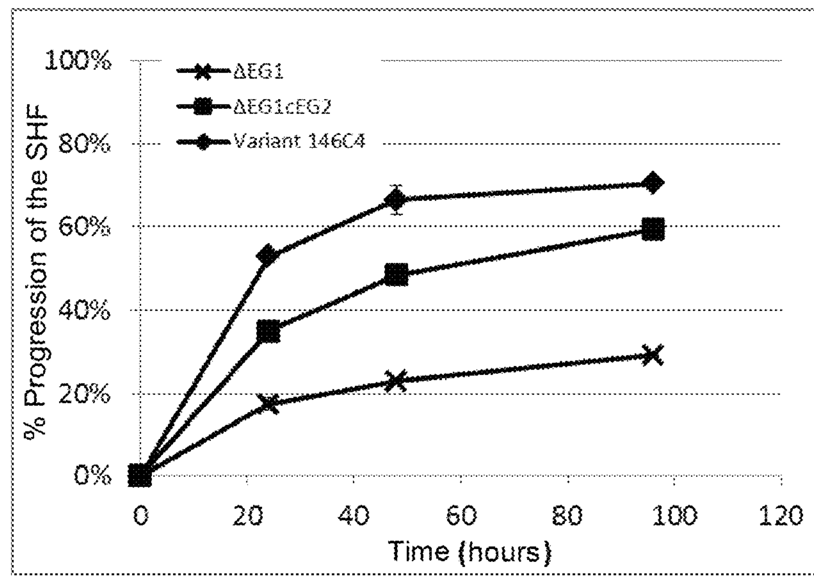
FIG. 3 is a graph presenting the results of SHF for the cocktail derived from the strain 146C4/7, a reference cocktail produced by the strain CL847 ΔEG1 (ΔEG1) supplemented with β-glucosidase and another reference cocktail produced by the strain CL847 ΔEG1 retransformed with the EG2 reference gene (ΔEG1cEG2) supplemented with β-glucosidase.

FIG. 3 presents the results of SHF for the cocktail resulting from the strain 146C4/7 (SEQ ID NO: 16).

The results presented in FIG. 3 show that the initial rate of hydrolysis of the cocktail produced by the 146C4 variant is greater than those of the ΔEG1 and ΔEG1cEG2 reference cocktails. The final hydrolysis yield is also greater than that of the ΔEG1 and ΔEG1cEG2 reference cocktails.

FIG. 4 presents the results of SHF for the cocktail resulting from the strain 222E1/1 (SEQ ID NO: 24) and the cocktail resulting from the strain 225C7/7 (SEQ ID NO: 26).

The results presented in FIG. 4 show that the initial rates of hydrolysis of the cocktails produced by the 222E1 variant and the 225C7 variant are greater than those of the ΔEG1 and ΔEG1cEG2 reference cocktails. The final hydrolysis yields are also greater than those of the ΔEG1 and ΔEG1cEG2 reference cocktails.

Example 6: Effectiveness of the Enzymes in Hydrolysis of Lignocellulosic Biomass According to an SSF Process The substrate used is the same as that described in table 6 (example 4).

The SSFs are carried out in triplicate in laboratory reactors. Said reactors consist of the following elements:

- a glass flask having a 30 ml working capacity;
- a polyether ether ketone (PEEK) safety stopper;
- a DV-118 one-way valve sold by the company Vaplock attached through the stopper. The valve is configured to open at the outlet when the relative pressure in the flask is greater than 70 mbar;
- a hollow polypropylene tube, fitted through a second, which passes through the stopper, and equipped at the lower end of said tube with a septum;
- a flat seal disposed between the neck of the flask and the stopper.

The principle for operating the bioreactors is the following: the $CO_2$ produced during the ethanolic fermentation accumulates in the top space located above the reaction medium, causing, by accumulation, an increase in the pressure in the bioreactor ($P_G$). When $P_G$ becomes greater than the pressure for opening the one-way valve ($P_S$), said valve opens to allow an amount of gas to escape, said amount being, for example, determined by weighing. When $P_G<P_S$, the valve closes again until $P_G$ is greater than $P_S$. Thus, the bioreactor when operating is always under pressure so as to ensure a stable anaerobic medium for the fermentation. The amount of ethanol produced is evaluated by the $CO_2$ production estimated by weight loss on the basis of the following stoichiometric equation for fermentation of glucose to ethanol:

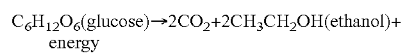

$$C_6H_{12}O_6(\text{glucose}) \rightarrow 2CO_2 + 2CH_3CH_2OH(\text{ethanol}) + \text{energy}$$

The culture medium used for the SSF is an aqueous medium which comprises:

- a 50 mM acetate buffer for pH 5;
- chloramphenicol at 0.1 g/l;

nutritive medium containing 3 g/l of $KH_2PO_4$, 2 g/l of $(NH_4)_2SO_4$, 0.4 g/l of $MgSO_4.7H_2O$ and 1 g/l of yeast extract.

The SSFs were carried out at 10±0.01% w/w of solids, i.e. an equivalent of 5.4% cellulose w/w for a total reaction mass of 15±0.003 g. The protein content is fixed at 10±0.01 mg of cellulases per gram of solids, i.e. approximately 19 mg/g of cellulose. The concentration of the enzymatic cocktails was measured by the Lowry method using BSA (Bovine Serum Albumin) as reference. Each cocktail was supplemented with β-glucosidase activity in an amount of 120±2 IU/g of cellulose, by adding SP188 β-glucosidase (Novozymes).

The sugar fermentation yeast (*Saccharomyces cerevisiae,* Ethanol Red strain, Fermentis, France) is added to the medium so as to obtain a content of 2±0.1 g/kg.

The enzymes and the yeasts are added to the bioreactors after one hour of conditioning of the wheat straw that has been pretreated at 35° C. with the buffer, the chloramphenicol and the culture medium.

The SSF reaction is carried out at a temperature of approximately 35° C., by placing the laboratory bioreactor in an Infors HT Multitron Standard incubator with an orbital rotation speed of 150 revolutions per minute.

Over time, the weight loss was monitored by weighing the bioreactors. At the end of the reaction, the fermentation must is heated at 100° C. for 5 minutes, cooled and centrifuged in order to separate the non-hydrolyzed solids from the fermentation liquor. The latter is then analyzed by gas chromatography in order to determine its ethanol concentration.

The cocktails resulting from example 4 were evaluated. Two control tests are carried out with the reference cocktails also supplemented with β-glucosidase for comparison: one produced by the strain CL847 ΔEG1 (ΔEG1) and one by the strain CL847 ΔEG1 retransformed with the EG2 reference gene (ΔEG1cEG2).

FIG. 5 presents the results of SSF for the cocktail resulting from the strain 146C4/7 and for the cocktail resulting from the strain 191H11/9 (SEQ ID NO 22):

The results presented in FIG. 5 show that the progressions (ethanol productions for the same dose of enzymes) of the SSF over the course of 100 hours for the cocktail expressing the 146C4 endoglucanase and the cocktail expressing the 191H11 endoglucanase are greater than those of the ΔEG1 and ΔEG1cEG2 reference cocktails.

FIG. 6 presents the results of SSF for the 3 cocktails resulting from the strains 222E1/1, 222E1/2 and 222E1/7 (average of the results obtained with the 2 variants) and for the cocktail resulting from the strain 225C7/7.

The results presented in FIG. 6 show that the progressions of the SSF over the course of 100 hours for the cocktail expressing the 222E1 endoglucanase and the cocktail expressing the 225C7 endoglucanase are equivalent and greater than those of the ΔEG1 and ΔEG1cEG2 reference cocktails.

The invention claimed is:

1. An isolated or purified polypeptide characterized in that it has an improved endoglucanase activity at 35° C. compared with the endoglucanase activity of the EG2 reference protein, said polypeptide being chosen from the group consisting of:

i) an amino acid sequence chosen from SEQ ID NO: 4, SEQ ID NO: 8, SEQ ID NO: 10, SEQ ID NO: 12; SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 and SEQ ID NO: 34; and ii) an amino acid sequence having a percentage identity of at least 98% relative to the sequence SEQ ID NO: 4, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 or SEQ ID NO: 34.

2. A purified or isolated nucleic acid characterized in that it encodes at least one polypeptide as claimed in claim 1.

3. The purified or isolated nucleic acid as claimed in claim 2, chosen from the following sequences: SEQ ID NO: 3, SEQ ID NO: 7, SEQ ID NO: 9, SEQ ID NO: 11; SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33.

4. A vector characterized in that it comprises a nucleic acid as claimed in claim 2.

5. An isolated host cell characterized in that it comprises the nucleic acid as claimed in claim 2.

6. The isolated host cell as claimed in claim 5, characterized in that it is chosen from *Trichoderma, Aspergillus, Neurospora, Humicola, Penicillium, Fusarium, Thermomonospora, Myceliophthora, Chrysosporium, Bacillus, Pseudomonas, Escherichia, Clostridium, Cellulomonas, Streptomyces, Yarrowia, Pichia* and *Saccharomyces.*

7. The isolated host cell as claimed in claim 5, characterized in that it is chosen from *Trichoderma reesei, Trichoderma viridae, Trichoderma koningii, Aspergillus niger, Aspergillus nidulans, Aspergillus wentii, Aspergillus oryzae, Aspergillus phoenicis, Neurospora crassa, Humicola grisae, Myceliophthora thermopila, Chrysosporium lucknowense, Penicillium pinophilum, Penicillium oxalicum, Escherichia coli, Clostridium acetobutylicum, Clostridium saccharolyticum, Clostridium benjerinckii, Clostridium butylicum, Pichia pastoris, Yarrowia lipolityca* and *Saccharomyces cerevisiae.*

8. A method for hydrolyzing cellulose comprising contacting a polypeptide of claim 1 with cellulose.

9. A method for producing biofuel comprising contacting a polypeptide of claim 1 with biomasse.

10. An enzymatic composition capable of acting on lignocellulosic biomass comprising at least one polypeptide as claimed in claim 1.

11. A process for producing biofuel from biomass, characterized in that it comprises the following successive steps:

suspension, in an aqueous phase, of the biomass to be hydrolyzed;

hydrolysis, in the presence of an enzymatic composition as claimed in claim 10, of the lignocellulosic biomass so as to produce a hydrolysate containing glucose;

fermentation of the glucose of the hydrolysate, in presence of a fermentative organism, so as to produce a fermentation must;

separation of the biofuel from the fermentation must.

12. A process for producing biofuel from biomass, characterized in that it comprises the following successive steps:

suspension, in an aqueous phase, of the biomass to be hydrolyzed;

simultaneous addition of an enzymatic composition as claimed in claim 10 and of a fermentative organism so as to produce a fermentation must;

separation of the biofuel from the fermentation must.

13. The process as claimed in claim 12, wherein the fermentative organism is chosen from a host cell comprising a nucleic acid encoding for at least one isolated or purified polypeptide which has an improved endoglucanase activity compared with the endoglucanase activity of the EG2 reference protein, said polypeptide being chosen from the group consisting of:

i) an amino acid sequence chosen from SEQ ID NO: 4, SEQ ID NO: 8, SEQ ID NO: 10, SEQ ID NO: 12; SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 and SEQ ID NO: 34; and ii) an amino acid sequence having a percentage identity of at least 98% relative to the sequence SEQ ID NO: 4, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 or SEQ ID NO: 34.

14. A process for producing biofuel from biomass comprising:

suspending, in an aqueous phase, the biomass to be hydrolyzed; adding one or more host cells comprising a nucleic acid encoding for at least one isolated or purified polypeptide has an improved endoglucanase activity compared with the endoglucanase activity of the EG2 reference protein, said polypeptide being chosen from the group consisting of:

i) an amino acid sequence chosen from SEQ ID NO: 4, SEQ ID NO: 8, SEQ ID NO: 10, SEQ ID NO: 12; SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 and SEQ ID NO: 34; and ii) an amino acid sequence having a percentage identity of at least 98%, relative to the sequence SEQ ID NO: 4, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 or SEQ ID NO: 34, with a fermentative organism and/or an enzymatic composition capable of acting on lignocellulosic biomass and comprising at least one isolated or purified polypeptide has an improved endoglucanase activity compared with the endoglucanase activity of the EG2 reference protein, said polypeptide being chosen from the group consisting of:

i) an amino acid sequence chosen from SEQ ID NO: 4, SEQ ID NO: 8, SEQ ID NO: 10, SEQ ID NO: 12; SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 and SEQ ID NO: 34; and ii) an amino acid sequence having a percentage identity of at least 98%, relative to the sequence SEQ ID NO: 4, SEQ ID NO: 14, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 or SEQ ID NO: 34, so as to produce a fermentation must; and separating the biofuel from the fermentation must.

15. An isolated host cell characterized in that it comprises the vector as claimed in claim 4.

16. A vector characterized in that it comprises a nucleic acid as claimed in claim 3.

17. An isolated host cell as claimed in claim 6, selected from the group consisting of *Trichoderma reesei, Trichoderma viridae, Trichoderma koningii, Aspergillus niger, Aspergillus nidulans, Aspergillus wentii, Aspergillus oryzae, Aspergillus phoenicis, Neurospora crassa, Humicola grisae, Myceliophthora thermopila, Chrysosporium lucknowense, Penicillium pinophilum, Penicillium oxalicum, Escherichia coli, Clostridium acetobutylicum, Clostridium saccharolyticum, Clostridium benjerinckii, Clostridium butylicum, Pichia pastoris, Yarrowia lipolityca* and *Saccharomyces cerevisiae.*

* * * * *